US008409208B2

(12) United States Patent
Abdou

(10) Patent No.: US 8,409,208 B2
(45) Date of Patent: Apr. 2, 2013

(54) DEVICE AND METHOD TO ACCESS THE ANTERIOR COLUMN OF THE SPINE

(76) Inventor: M. Samy Abdou, San Diego, CA (US)

( * ) Notice: Subject to any disclaimer, the term of this patent is extended or adjusted under 35 U.S.C. 154(b) by 305 days.

(21) Appl. No.: 12/573,813

(22) Filed: Oct. 5, 2009

(65) Prior Publication Data

US 2010/0087878 A1  Apr. 8, 2010

Related U.S. Application Data

(60) Provisional application No. 61/195,191, filed on Oct. 4, 2008.

(51) Int. Cl.
*A61B 17/56* (2006.01)

(52) U.S. Cl. ..................................... 606/86 R

(58) Field of Classification Search .......... 606/60, 606/86 R, 246–279; 623/17.11–17.16
See application file for complete search history.

(56) References Cited

U.S. PATENT DOCUMENTS

| | | | |
|---|---|---|---|
| 2,248,054 A | 7/1941 | Becker | |
| 3,659,595 A | 5/1972 | Haboush | |
| 3,695,259 A | 10/1972 | Yost | |
| 3,741,205 A | 6/1973 | Markolf et al. | |
| 4,175,555 A * | 11/1979 | Herbert | 606/304 |
| 4,289,123 A | 9/1981 | Dunn | |
| 4,488,543 A | 12/1984 | Tornier | |
| 4,493,317 A | 1/1985 | Klaue | |
| 4,503,848 A | 3/1985 | Caspar et al. | |
| 4,794,918 A | 1/1989 | Wolter | |
| 4,938,769 A | 7/1990 | Shaw | |
| 4,944,757 A | 7/1990 | Martinez et al. | |
| 4,957,497 A | 9/1990 | Hoogland et al. | |
| 4,963,152 A | 10/1990 | Hofmann et al. | |
| 5,061,271 A | 10/1991 | Van Zile | |
| 5,127,914 A | 7/1992 | Calderale et al. | |
| 5,133,717 A | 7/1992 | Chopin | |
| 5,147,361 A | 9/1992 | Ojima et al. | |
| 5,180,381 A | 1/1993 | Aust et al. | |
| 5,324,290 A | 6/1994 | Zdeblick et al. | |
| 5,354,292 A | 10/1994 | Braeuer et al. | |
| 5,364,399 A | 11/1994 | Lowery et al. | |
| 5,397,363 A | 3/1995 | Gelbard | |
| 5,545,164 A | 8/1996 | Howland | |
| 5,578,034 A | 11/1996 | Estes | |
| 5,616,142 A | 4/1997 | Yuan et al. | |
| 5,676,666 A | 10/1997 | Oxland et al. | |

(Continued)

FOREIGN PATENT DOCUMENTS

| | | |
|---|---|---|
| WO | 95/25474 | 9/1995 |
| WO | 97/37620 | 10/1997 |

(Continued)

OTHER PUBLICATIONS

Denis, F. "The three column spine and its significance in the classification of acute thoracolumbar spinal injuries" Spine Nov.-Dec. 1983; 8(8):817-831.

(Continued)

*Primary Examiner* — Kevin T Truong
*Assistant Examiner* — Christopher Beccia
(74) *Attorney, Agent, or Firm* — Gazdzinski & Associates, P.C.

(57) ABSTRACT

Methods and devices are configured to permit a surgeon to access the anterior column of the spine without significant manipulation of intervening nerve elements.

22 Claims, 23 Drawing Sheets

U.S. PATENT DOCUMENTS

| | | | |
|---|---|---|---|
| 5,681,311 A | 10/1997 | Foley et al. | |
| 5,681,312 A | 10/1997 | Yuan et al. | |
| 5,713,900 A * | 2/1998 | Benzel et al. | 606/250 |
| 5,735,853 A | 4/1998 | Olerud | |
| 5,928,233 A | 7/1999 | Apfelbaum et al. | |
| 5,954,722 A | 9/1999 | Bono | |
| 5,971,987 A | 10/1999 | Huxel et al. | |
| 5,993,449 A | 11/1999 | Schlapfer et al. | |
| 6,039,740 A | 3/2000 | Olerud | |
| 6,139,549 A | 10/2000 | Keller | |
| 6,152,927 A | 11/2000 | Farris et al. | |
| D440,311 S | 4/2001 | Michelson | |
| 6,224,602 B1 | 5/2001 | Hayes | |
| 6,235,034 B1 | 5/2001 | Bray | |
| D449,692 S | 10/2001 | Michelson | |
| 6,306,136 B1 | 10/2001 | Baccelli | |
| 6,565,571 B1 | 5/2003 | Jackowski et al. | |
| 6,599,290 B2 | 7/2003 | Bailey et al. | |
| 6,793,658 B2 | 9/2004 | Le Huec et al. | |
| 6,852,128 B2 | 2/2005 | Lange | |
| 6,884,242 B2 | 4/2005 | Le Huec et al. | |
| 7,060,066 B2 * | 6/2006 | Zhao et al. | 606/279 |
| 7,309,338 B2 * | 12/2007 | Cragg | 606/80 |
| 7,527,640 B2 | 5/2009 | Ziolo et al. | |
| 7,909,871 B2 * | 3/2011 | Abdou | 623/17.11 |
| 2003/0195518 A1 * | 10/2003 | Cragg | 606/80 |
| 2004/0073216 A1 * | 4/2004 | Lieberman | 606/61 |
| 2005/0137604 A1 * | 6/2005 | Assell et al. | 606/93 |
| 2005/0177167 A1 * | 8/2005 | Muckter | 606/73 |
| 2006/0058800 A1 * | 3/2006 | Ainsworth et al. | 606/72 |

FOREIGN PATENT DOCUMENTS

| | | |
|---|---|---|
| WO | 99/04718 | 2/1999 |
| WO | 99/21502 | 5/1999 |
| WO | 99/56653 | 11/1999 |
| WO | 00/24325 | 5/2000 |
| WO | 00/78238 | 12/2000 |

OTHER PUBLICATIONS

Marotta et al., "A novel minimally invasive pre-sacral approach and instrumentation technique for anterior L5/S1 intervertebral discectomy and fusion" *Neurosurg. Focus* 20(1): E9, 2006.

\* cited by examiner

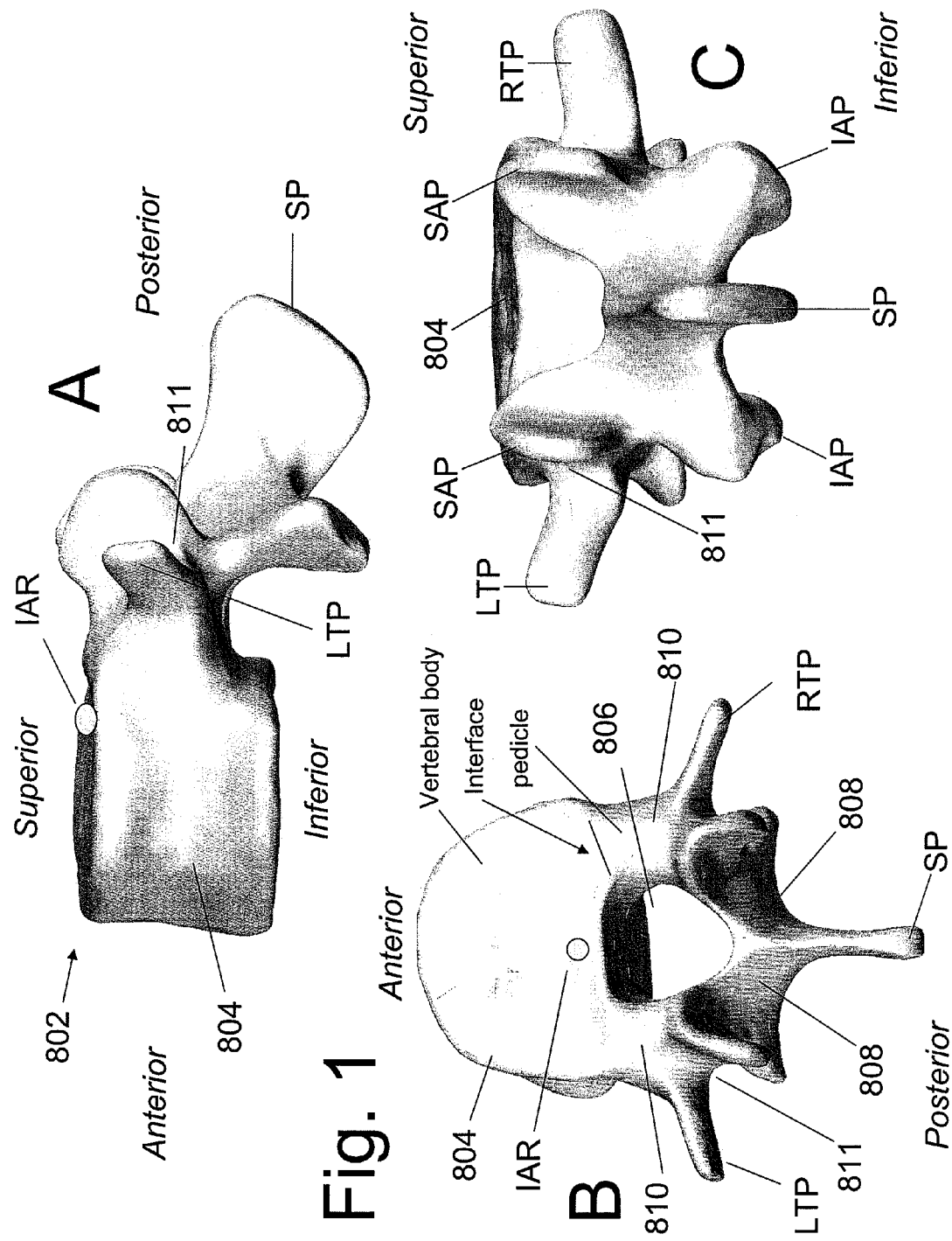

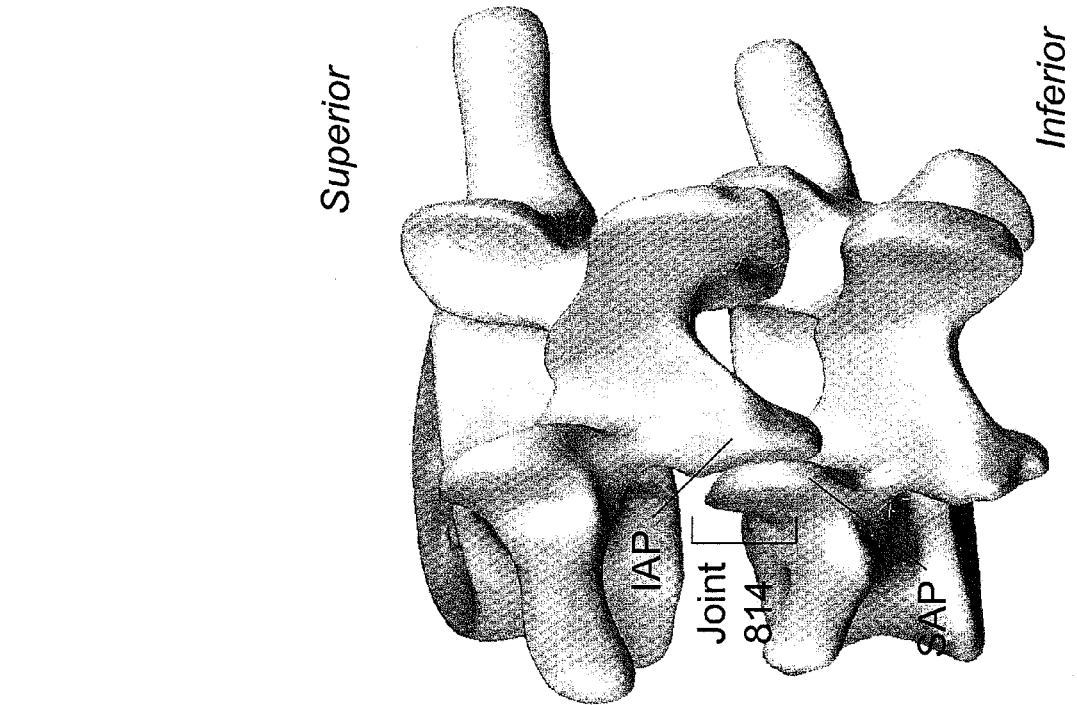
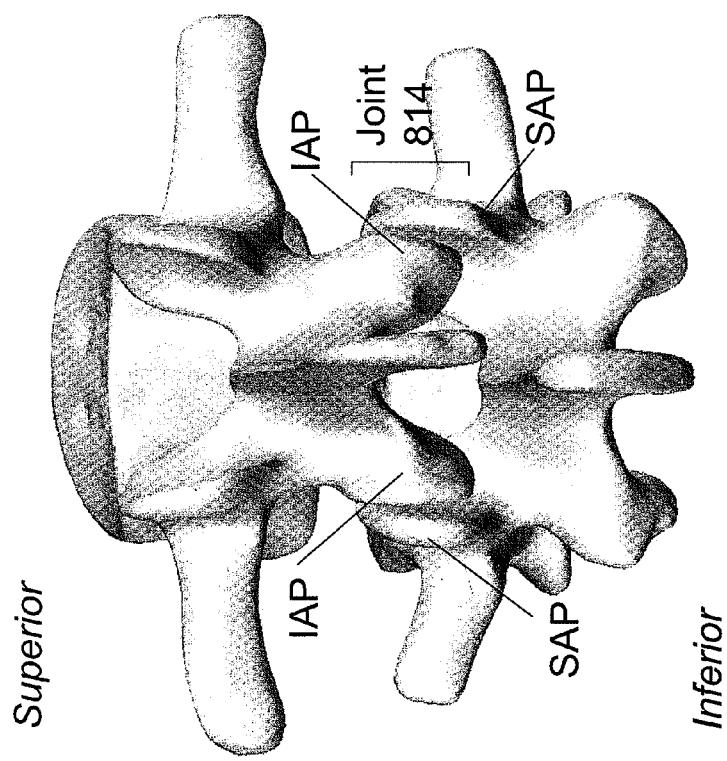

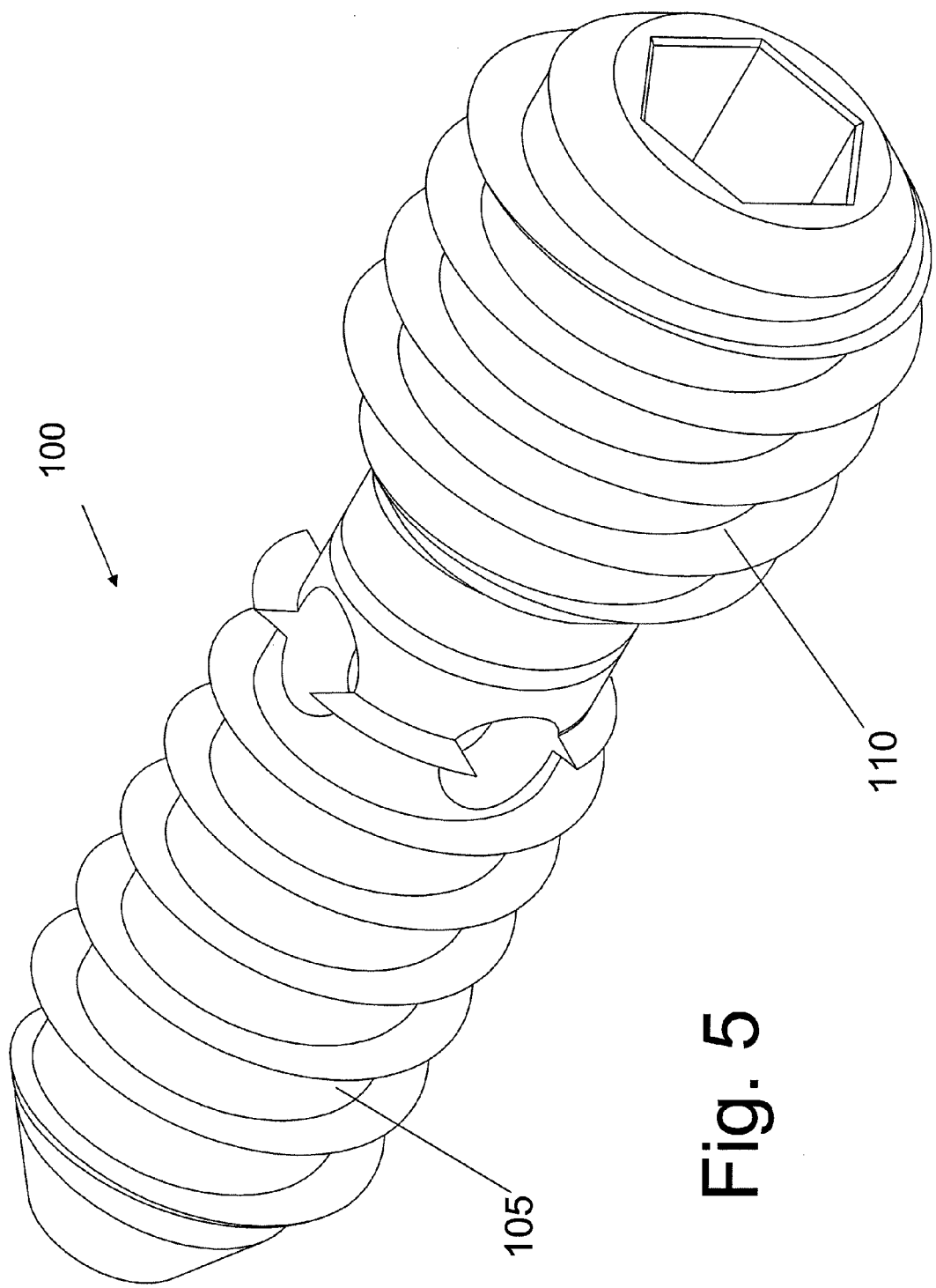

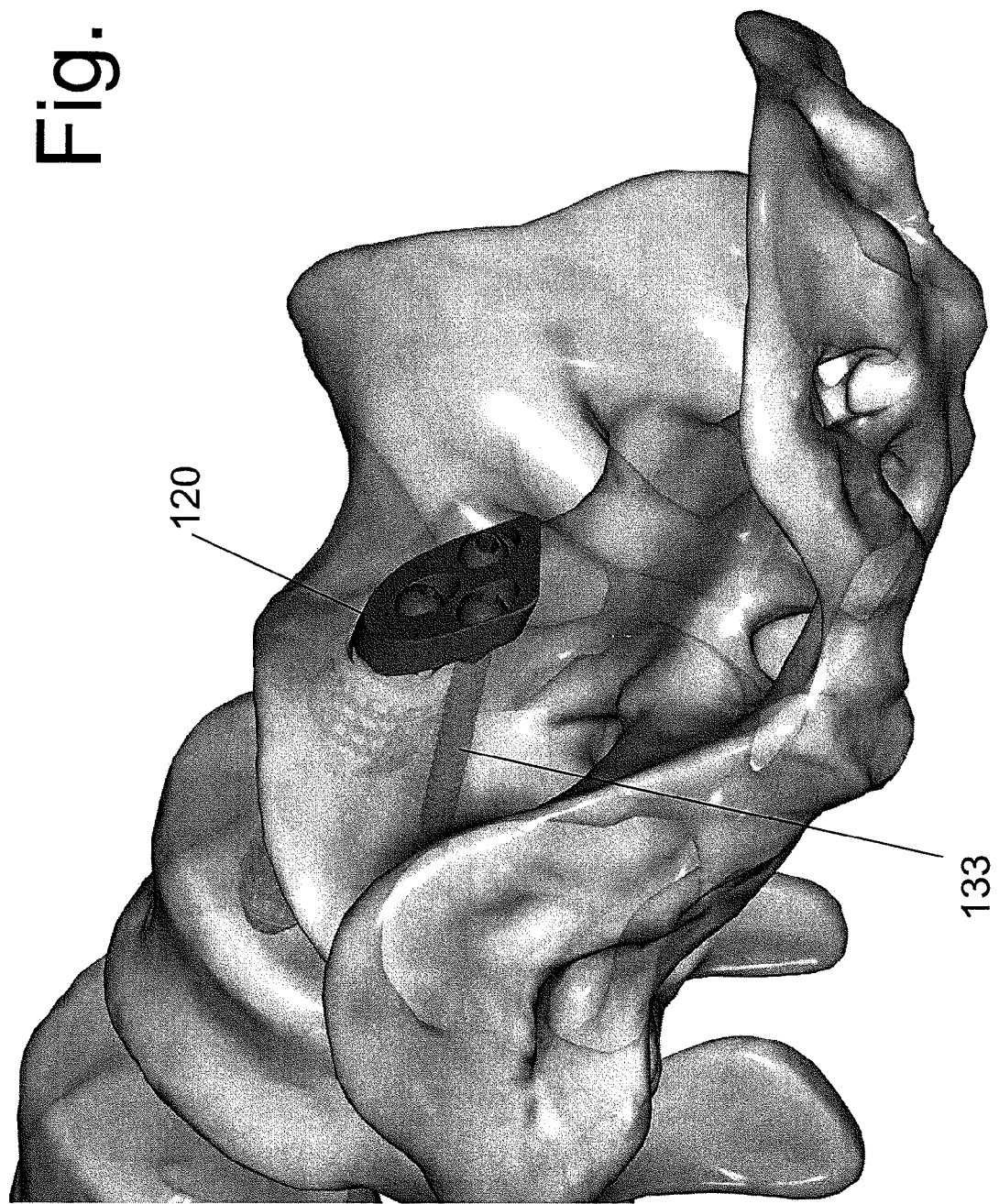

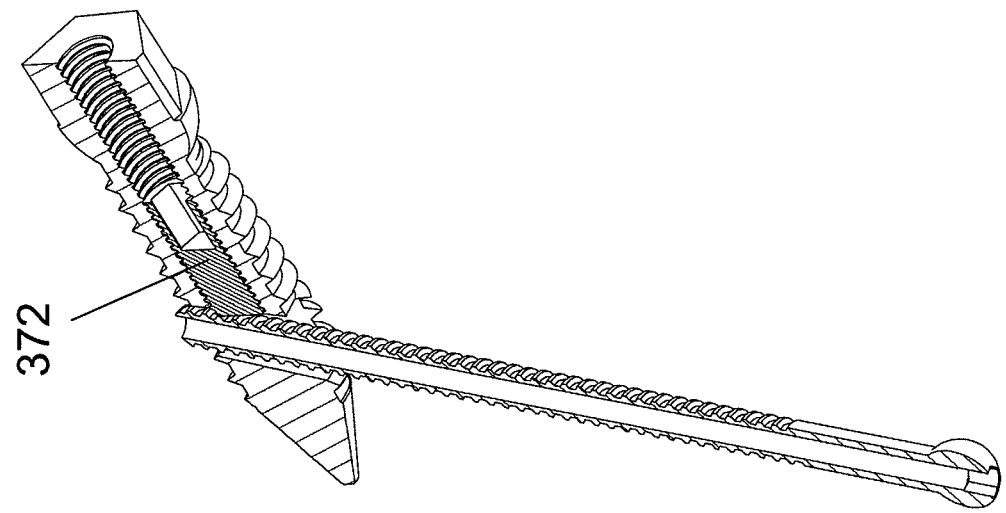
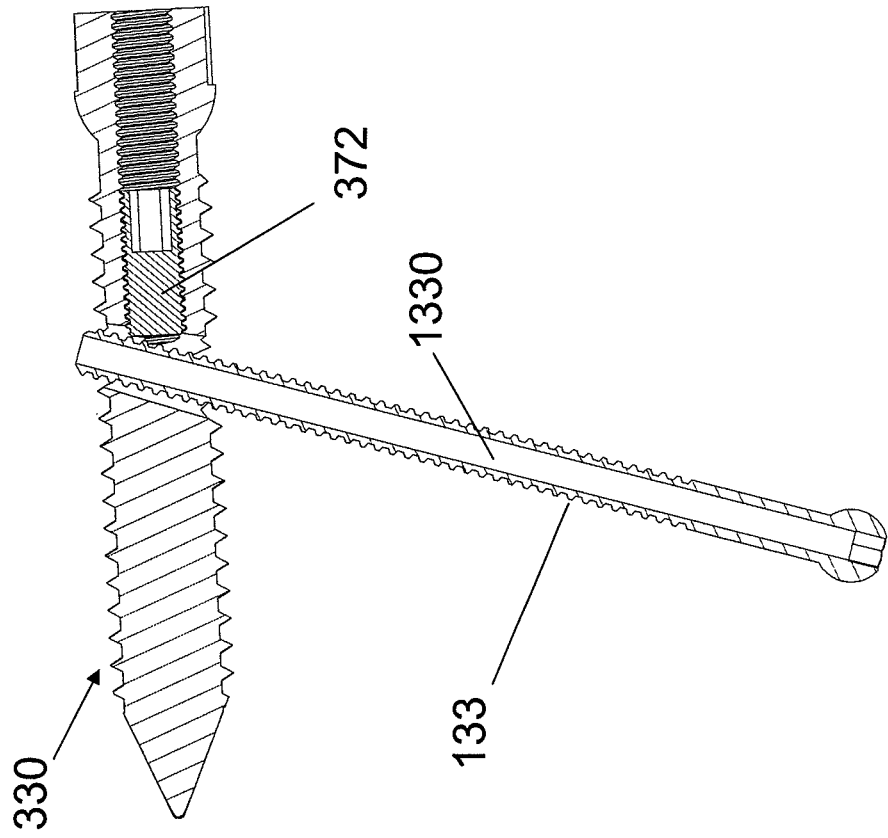
Fig. 22

DEVICE AND METHOD TO ACCESS THE ANTERIOR COLUMN OF THE SPINE

REFERENCE TO PRIORITY DOCUMENTS

This application claims priority of co-pending U.S. Provisional Patent Application Ser. No. 61/195,191, filed Oct. 4, 2008. Priority of the aforementioned filing date is hereby claimed and the disclosure of the Provisional Patent Application is hereby incorporated by reference in its entirety.

BACKGROUND

The surgical reconstruction of the bony skeleton is a common procedure in current medical practice. Regardless of the anatomical region or the specifics of the reconstructive procedure, many surgeons employ an implantable device that can adjust, align and maintain the spatial relationship(s) between adjacent bones. An extensive array of surgical techniques and implantable devices have been formulated to accomplish this goal.

Symptomatic degeneration of the lumbar spine occurs most commonly at the L4/5 and L5/S1 levels and fusion of one or both of these segments has emerged as a common surgical procedure. Currently, these vertebral bodies may be fused using an anterior, lateral or posterior approach and each has particular advantages and draw backs. Frequently, circumferential fusion of the unstable level with fixation of both the anterior and posterior aspect of the spine is desired. This requires that patients undergo a combination of the aforementioned approaches. The anterior or lateral approaches are used to insert the bone graft into the disc space between the adjacent vertebras while the posterior approach is used to place bone screws or similar fasteners that are used to immobilize the vertebral bodies.

Access to the disc space for bone graft placement requires dissection through the vital tissues that lie anterior or lateral to the spine. U.S. Pat. No. 7,309,338 and others disclose a method for the access of the anterior column of the lumbar spine using a pre-sacral approach. (U.S. Pat. No. 7,309,338 is hereby incorporated by reference in its entirety.) The procedure has been popularized by the corporation TranS1, Inc of Wilmington, N.C. as the "AXLIF" procedure. The technology for both the L5 to S1 fusion procedure and the L4 to S1 fusion procedure are described on the web site "www.trans1.com". All contents and disclosures of the web site are hereby incorporated by reference in their entirety. The procedure is further described in the article: *A novel minimally invasive pre-sacral approach and instrumentation technique for anterior L5/S1 intervertebral discectomy and fusion*. By Marotta et al., Neurosurg. Focus 20 (1): E9, 2006. The article is hereby incorporated by reference in its entirety.

With experience, an important shortcoming of the "AXLIF" procedure has been discovered. The procedure, which entails placement of a threaded screw or a threaded rod through an anterior segment of the sacrum and into the superior vertebral bones, fails to provide adequate segmental fixation in rotation and other planes of spinal motion. Thus, the "AXLIF" procedure must be supplemented with additional screw and orthopedic device stabilization in order to adequately immobilize the operative segment. Most commonly, posterior screw/rod fixation into the pedicle portion of the vertebral bones is used to supplement the "AXLIF" procedure. Unfortunately, the need to provide supplement fixation through alternative surgical corridors, such as the posterior approach to the spine, greatly limits the usefulness of the "AXLIF" procedure and obviates the advantages that the procedure provides over other current art.

SUMMARY

It is a goal of the present disclosure to supplement the "AXLIF" procedure with additional fixation placed onto the sacrum and vertebral bodies of superior bones through a pre-sacral surgical corridor. The pre-sacral surgical corridor designates a soft tissue corridor developed onto the anterior surface of the sacrum and extending from a skin incision at about the level of the coccyx and extending cephalad to at least the level of the S3 vertebral bone. In this way, the need for additional fixation onto the posterior aspect of the lumbar spine is minimized.

Other features and advantages should be apparent from the following description of various embodiments, which illustrate, by way of example, the principles of the disclosed devices and methods.

BRIEF DESCRIPTION OF THE DRAWINGS

FIG. 1 shows a diagrammatic representation of a spinal vertebral bone in multiple views.

FIG. 2A shows the posterior surface of adjacent vertebrae and the articulations between the vertebrae.

FIG. 2B shows an oblique view of the vertebrae.

FIG. 5 shows an embodiment of a threaded screw.

FIGS. 10, 11A and 11B show the plate implanted onto the surface of the anterior bony surface of the sacrum.

FIG. 22 shows sectional views of joined screw and an additional anchor assembly without the bone elements.

DETAILED DESCRIPTION

Figure 3:
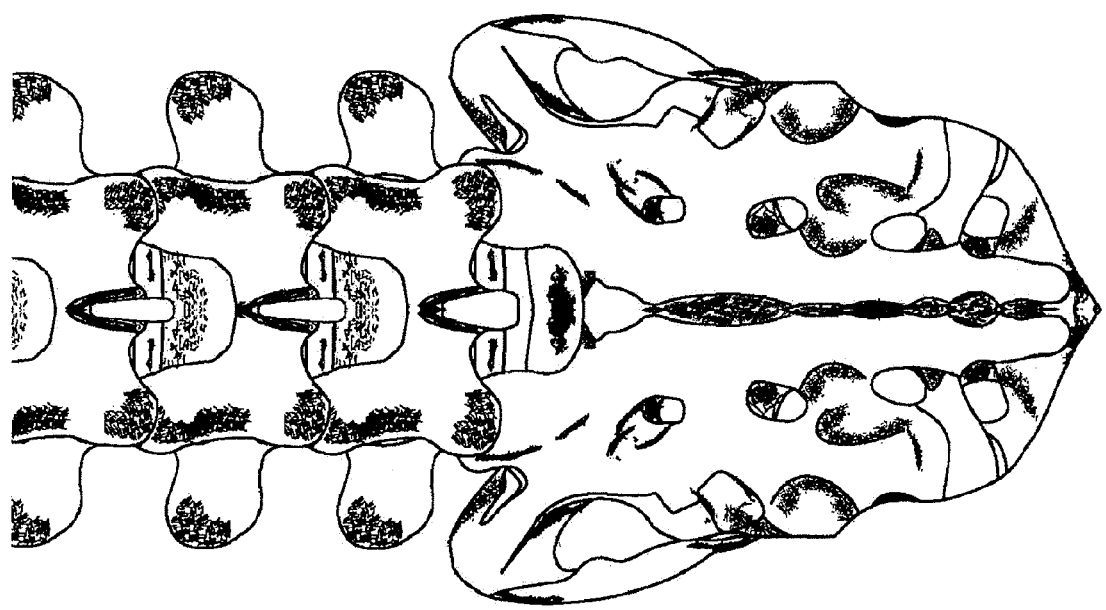
FIG. 3 shows a posterior view of the sacrum.

In order to promote an understanding of the principals of the disclosure, reference is made to the drawings and the embodiments illustrated therein. Nevertheless, it will be understood that the drawings are illustrative and no limitation of the scope of the invention is thereby intended. Any such alterations and further modifications in the illustrated embodiments, and any such further applications of the principles of the invention as illustrated herein are contemplated as would normally occur to one of ordinary skill in the art.

FIG. 1 shows a diagrammatic representation of a spinal vertebral bone 802 in multiple views. For clarity of illustration, the vertebral bone of FIG. 1 and those of other illustrations presented in this application are represented schematically and those skilled in the art will appreciate that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation.

Vertebral bone 802 contains an anteriorly-placed vertebral body 804, a centrally placed spinal canal and 806 and posteriorly-placed lamina 808. The pedicle (810) segments of vertebral bone 802 form the lateral aspect of the spinal canal and connect the laminas 808 to the vertebral body 804. The spinal canal contains neural structures such as the spinal cord and/or nerves. A midline protrusion termed the spinous process (SP) extends posteriorly from the medial aspect of laminas 808. A protrusion extends laterally from each side of the posterior aspect of the vertebral bone and is termed the transverse process (TP). A right transverse process (RTP) extends to the right and a left transverse process (LTP) extends to the left. A superior protrusion extends superiorly above the lamina on each side of the vertebral midline and is termed the superior articulating process (SAP). An inferior protrusion extends inferiorly below the lamina on each side of the vertebral midline and is termed the inferior articulating process (IAP). Note that the posterior aspect of the pedicle can be accessed at an indentation 811 in the vertebral bone between the lateral aspect of the SAP and the medial aspect of the transverse process (TP). In surgery, it is common practice to anchor a bone fastener into the pedicle portion of a vertebral bone by inserting the fastener through indentation 811 and into the underlying pedicle.

FIGS. 2A and 2B illustrate a functional spinal unit (FSU), which includes two adjacent vertebrae and the intervertebral disc between them. The intervertebral disc resides between the inferior surface of the upper vertebral body and the superior surface of the lower vertebral body. (Note that a space is shown in FIGS. 2A and 2B where intervertebral disc would reside.) FIG. 2A shows the posterior surface of the adjacent vertebrae and the articulations between them while FIG. 2B shows an oblique view. Note that FSU contains a three joint complex between the two vertebral bones, with the intervertebral disc comprising the anterior joint. The posterior joints include a facet joint 814 on each side of the midline, wherein the facet joint contains the articulation between the IAP of the superior vertebral bone and the SAP of the inferior bone. Movement between a superior and inferior vertebral bone of a functional spinal unit (FSU) occurs about a center of rotation (termed IAR, see FIG. 1) that is located within the posterior aspect of the vertebral body (but anterior to the spinal canal) and near the superior surface of the inferior vertebral body.

The preceding illustrations and definitions of anatomical structures are known to those of ordinary skill in the art. They are described in more detail in *Atlas of Human Anatomy*, by Frank Netter, third edition, Icon Learning Systems, Teterboro, N.J. The text is hereby incorporated by reference in its entirety.

Disclosed are methods and devices that permit a surgeon to access the anterior column of the spine without significant manipulation of the intervening nerve elements. (The "anterior column" is used here to designate that portion of the vertebral body and/or FSU that is situated anterior to the posterior longitudinal ligament. Thus, its use in this application encompasses both the anterior and middle column of Denis. See *The three column spine and its significance in the classification of acute thoracolumbar spinal injuries.* By Denis, F. Spine 1983 November-December; 8(8):817-31. The article is incorporated by reference in its entirety.)

Figure 4B:
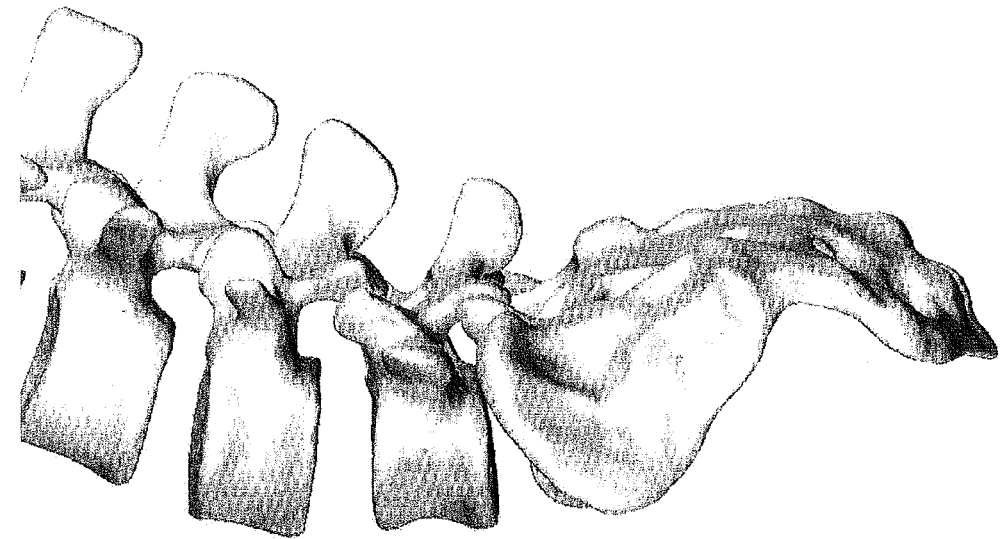
FIG. 4B shows a lateral view of the sacrum.
Figure 4A:
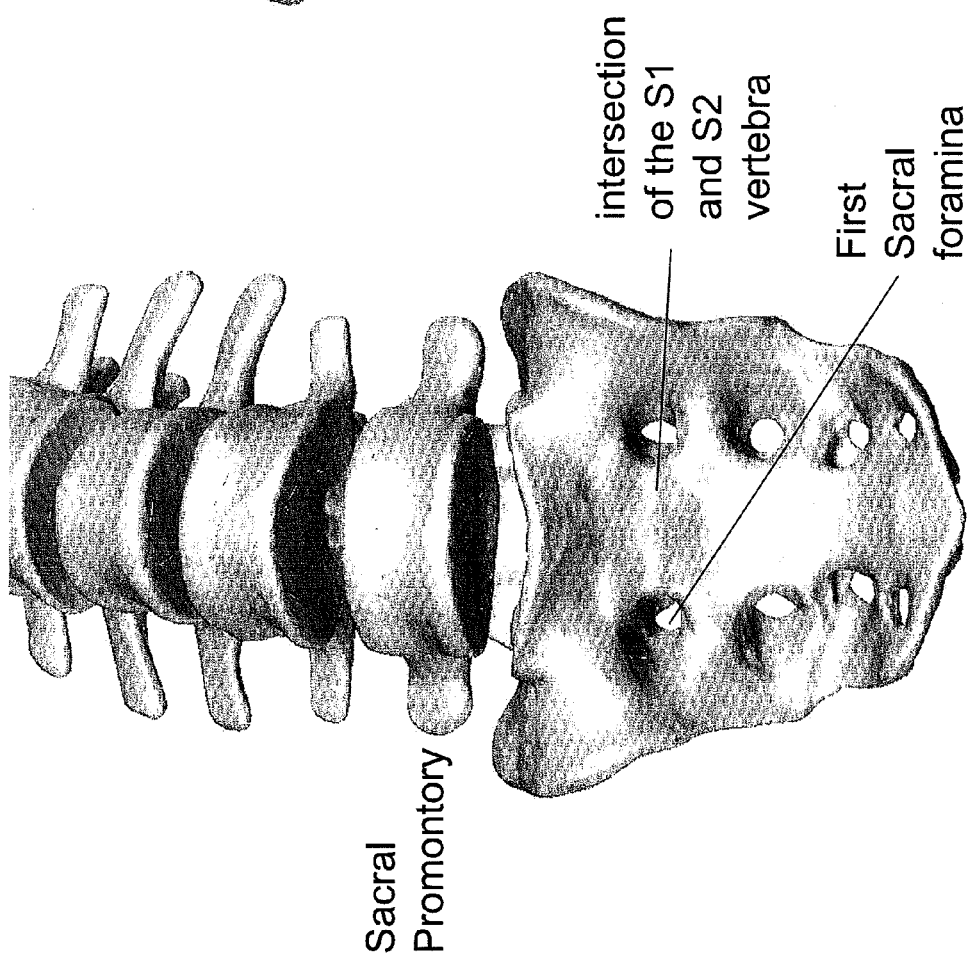
FIG. 4A shows an anterior view of the sacrum.

FIG. 3 shows a posterior view of the sacrum. FIG. 4A shows an anterior view and FIG. 4B shows a lateral view. The sacral promontory, sacral foramina, the S1/S2 vertebral intersection as well as other anatomical features are illustrated. Additional features of the sacrum are described in more detail in *Atlas of Human Anatomy*, by Frank Netter, third edition, Icon Learning Systems, Teterboro, N.J. The text is hereby incorporated by reference in its entirety.

The "AXLIF" procedure is more fully described within the previously listed and incorporated article and web site. An abbreviated description of the procedure follows and those of ordinary skill in the art will understand that the description does not fully recite all of the features and operative steps of the "AXLIF" procedure.

A skin incision is placed lateral to and at the approximate level of the coccyx. The surgeon's finger is used to bluntly dissect the colon and other soft tissues away from the anterior surface of the sacrum. Blunt dissection is continued with finger and instrument dissection until the anterior aspect of the S1 and S2 bones are reached. The anterior bony surface of the sacrum is entered at approximately the level of the intersection of the lower aspect of S1 and the superior aspect of S2. A hole is drilled through the S1 body portion of the sacrum and advanced into the L5/S1 disc space. An L5/S1 discectomy is performed through the formed sacral bore hole and the disc space is packed with bone graft or bone graft substitute. Preferably, the totality of the procedure is performed in a percutaneous manner, under X-ray guidance and through specifically designed hollow tubes. The bore hole is extended into the L5 vertebral body and a threaded screw is placed into the S1 body, across the L5/S1 disc space and into the L5 vertebral body. (See the previously listed referenced and incorporated web site and article for a full description of the "AXLIF" procedure).

Figure 6:
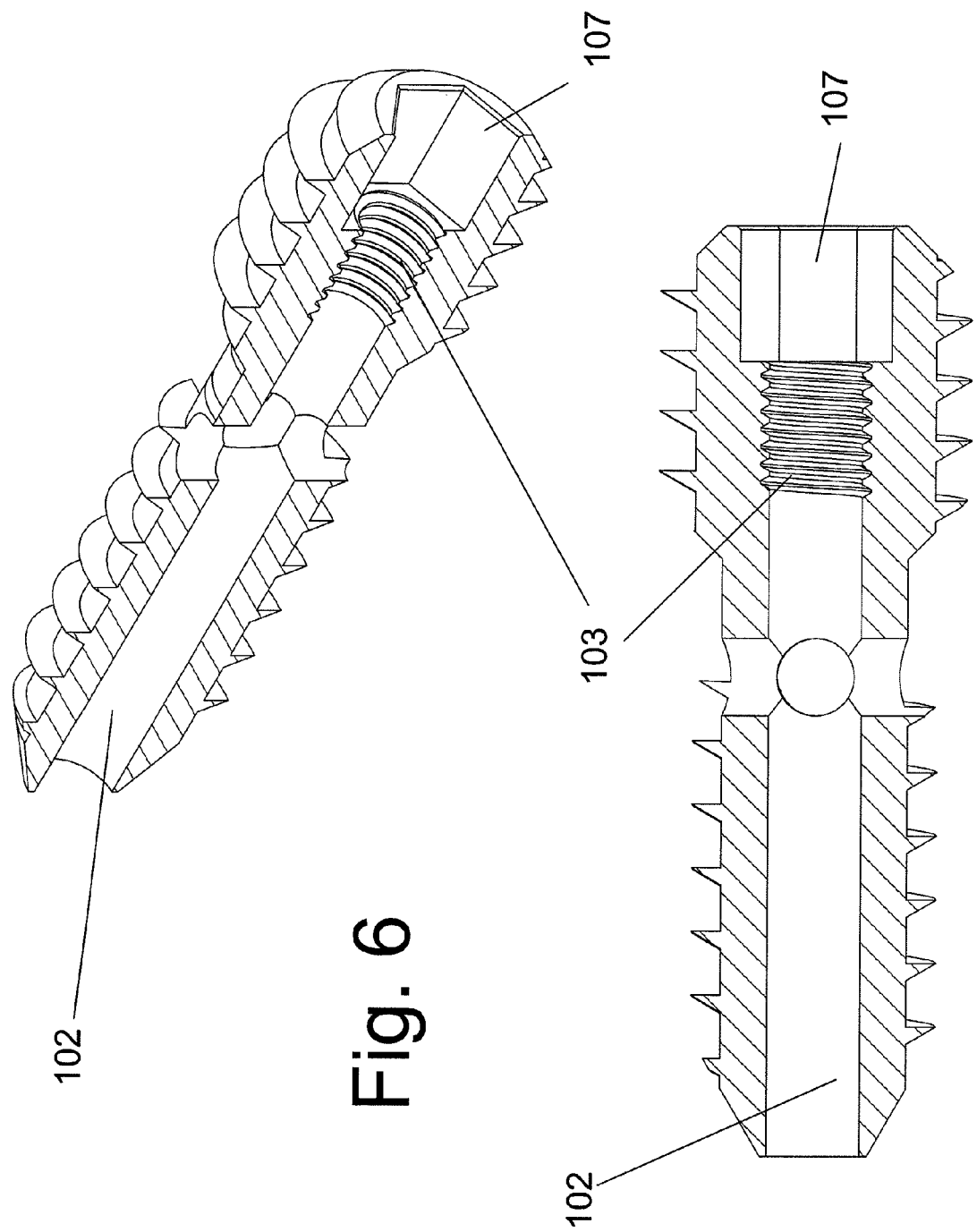
FIG. 6 shows sectional views of the screw.
Figure 7:
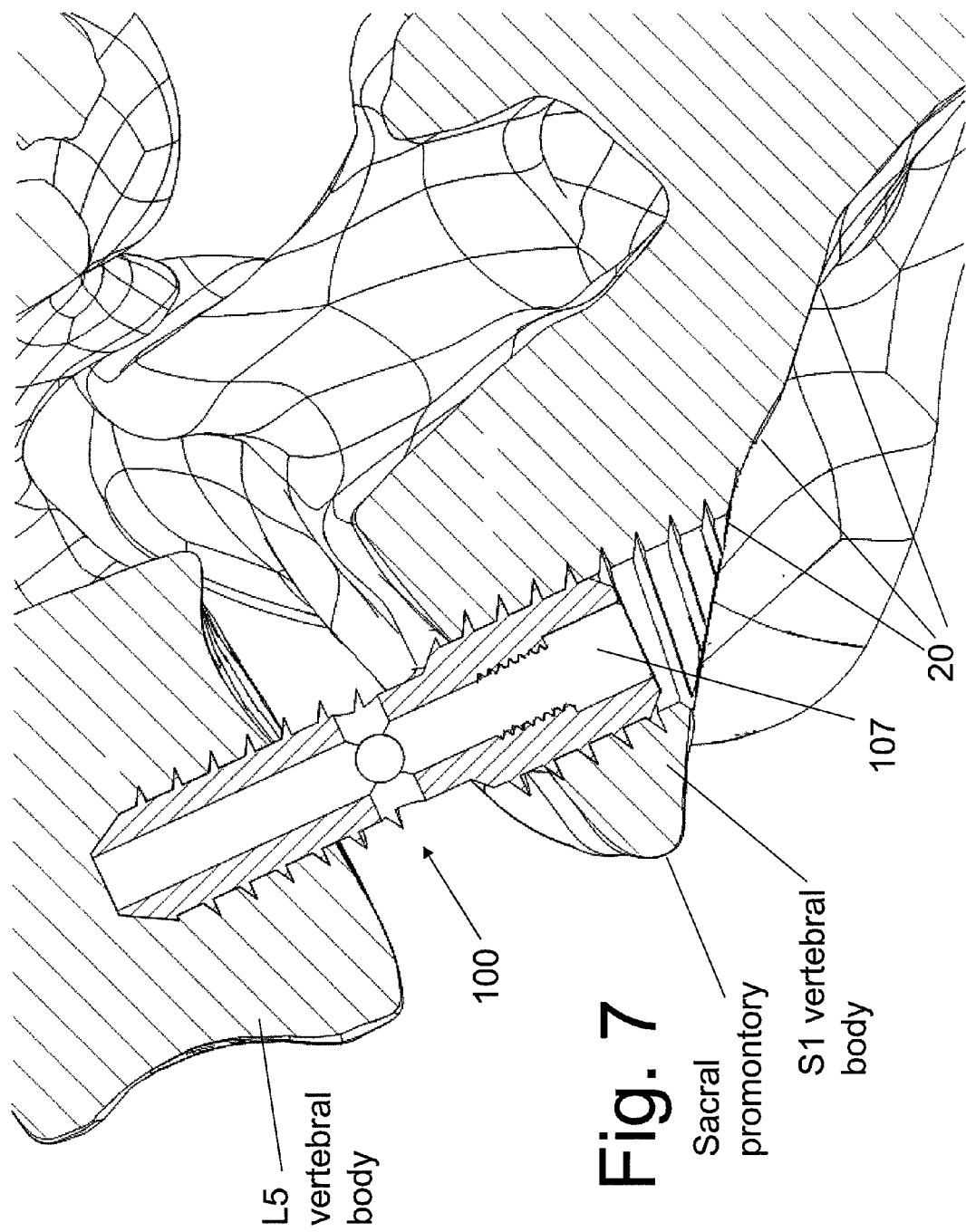
FIG. 7 shows an implanted screw.

An embodiment of the threaded screw is shown in a perspective view in FIG. 5. FIG. 6 shows sectional views of the screw. The screw 100 contains a first threaded segment 105 and a second threaded segment 110, wherein the threads of each segment are like-handed but of different pitch. (Further, segment 105 is preferably of lesser diameter than segment 110.) With advancement of the screw, segment 105 comes to rest within the L5 vertebral body while segment 110 comes to rest within the S1 vertebral body (FIG. 7). The threads of each of the two segments are of different pitch so that advancement of the screw within the vertebral bones produces a distraction force between the two vertebral bones and distracts the L5 and S1 vertebral bodies away from one another. Screws of different pitch segments are known in the art and have been used to produce distraction or compressive forces across bones. U.S. Pat. No. 4,175,555 granted to Timothy Herbert discloses a bone screw of variable thread segments. The patent is hereby incorporated by reference in its entirety. Screw 100 of the current disclosure is of similar design.

An internal bore 102 rests within screw 100 and contains threaded segment 103. Hex drive segment 107 is located on an end of internal bore 102 of screw 100. Segment 107 is used to engage a hex-ended screw driver (not shown), wherein the driver is adapted to rotate and drive screw 100 into bone. FIG. 7 illustrates a sectional view of the screw 100 within the L5 and S1 vertebral bodies. Note that the entry point for screw 100 is along the anterior bony surface 20 of the sacrum, at or about the intersection of the inferior aspect of S1 and superior aspect of S2.

Figure 8:
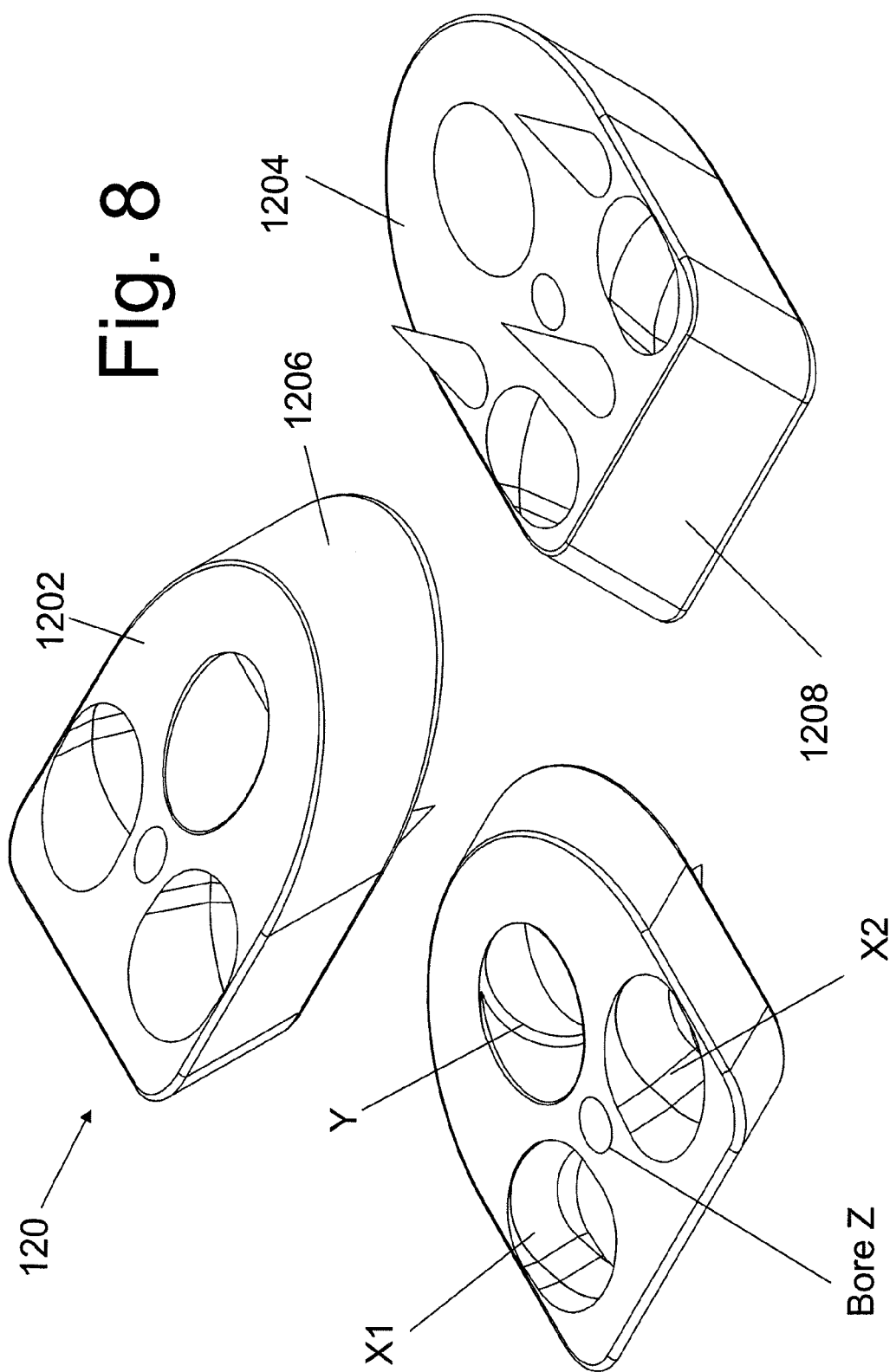
FIGS. 8 and 9 show a bone plate.
Figure 9:
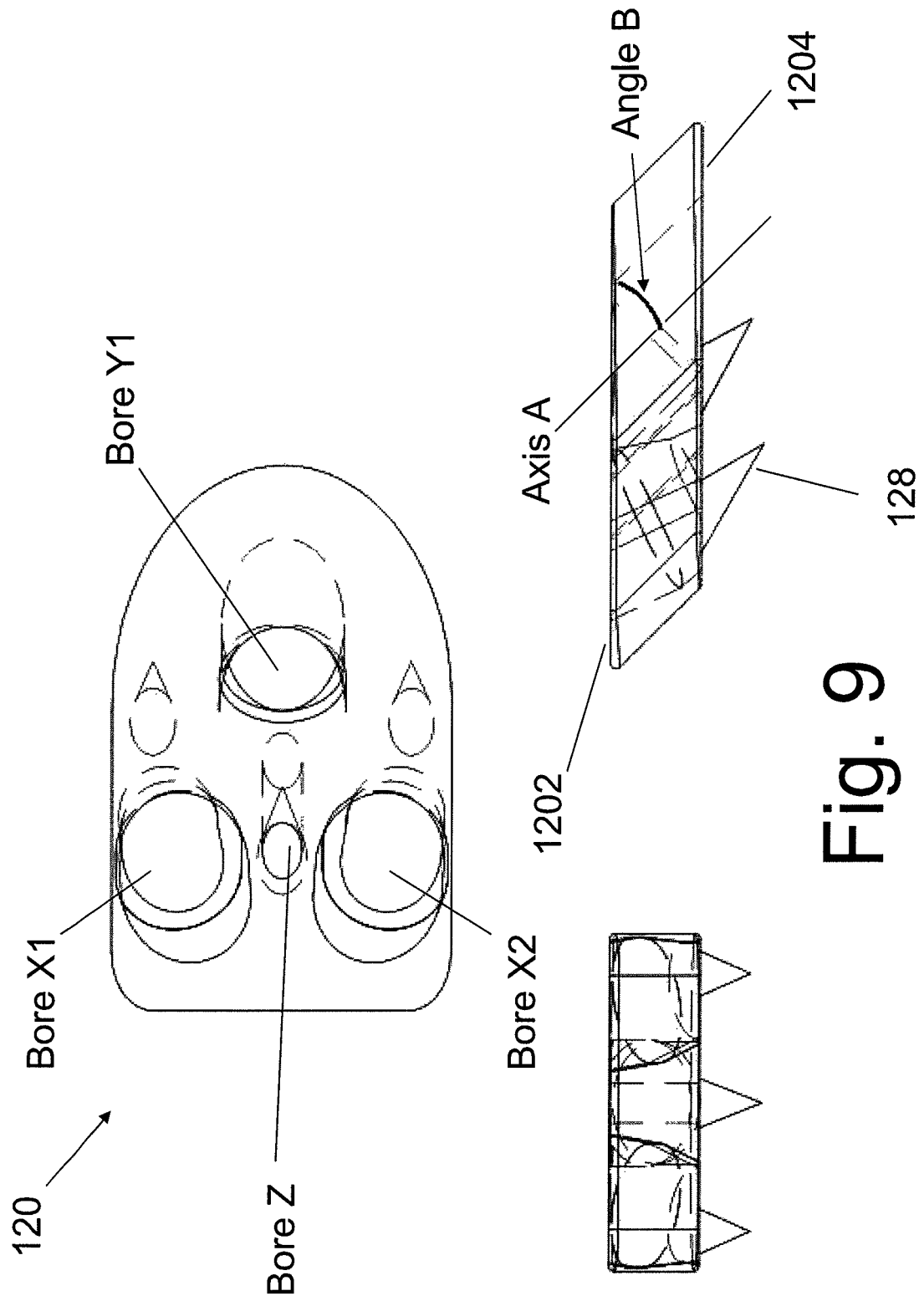

Plate 120 is shown in FIGS. 8 and 9. Plate 120 may contain a top surface 1202, a bottom surface 1204, and side surfaces that include an upper side surface 1206 and a lower side surface 1208. The plate further contains multiple bore holes that extend from top surface 1202 to bottom surface 1204. Each bore hole may be angled so that the long axis "A" of each bore hole is not perpendicular to top surface 1202 of plate 120. The long axis of each bore hole may form an angle "B" of 10 to 80 degrees with surface 1202. Further, the long axis of each of the inferior bore holes X1 and X2 are angled away for one another so that the shank of a screw placed into bore hole X1 and the shank of a screw placed into bore hole X2 will diverge from each other. That is, the distance between the distal tip of each screw shank is greater than the distance between the head portion of each screw. The bottom surface 1204 of the plate 120 preferably contains sharpened protrusions 128, wherein the protrusions are preferably angled relative to surface 1204—as shown in FIG. 9.

Figure 12:
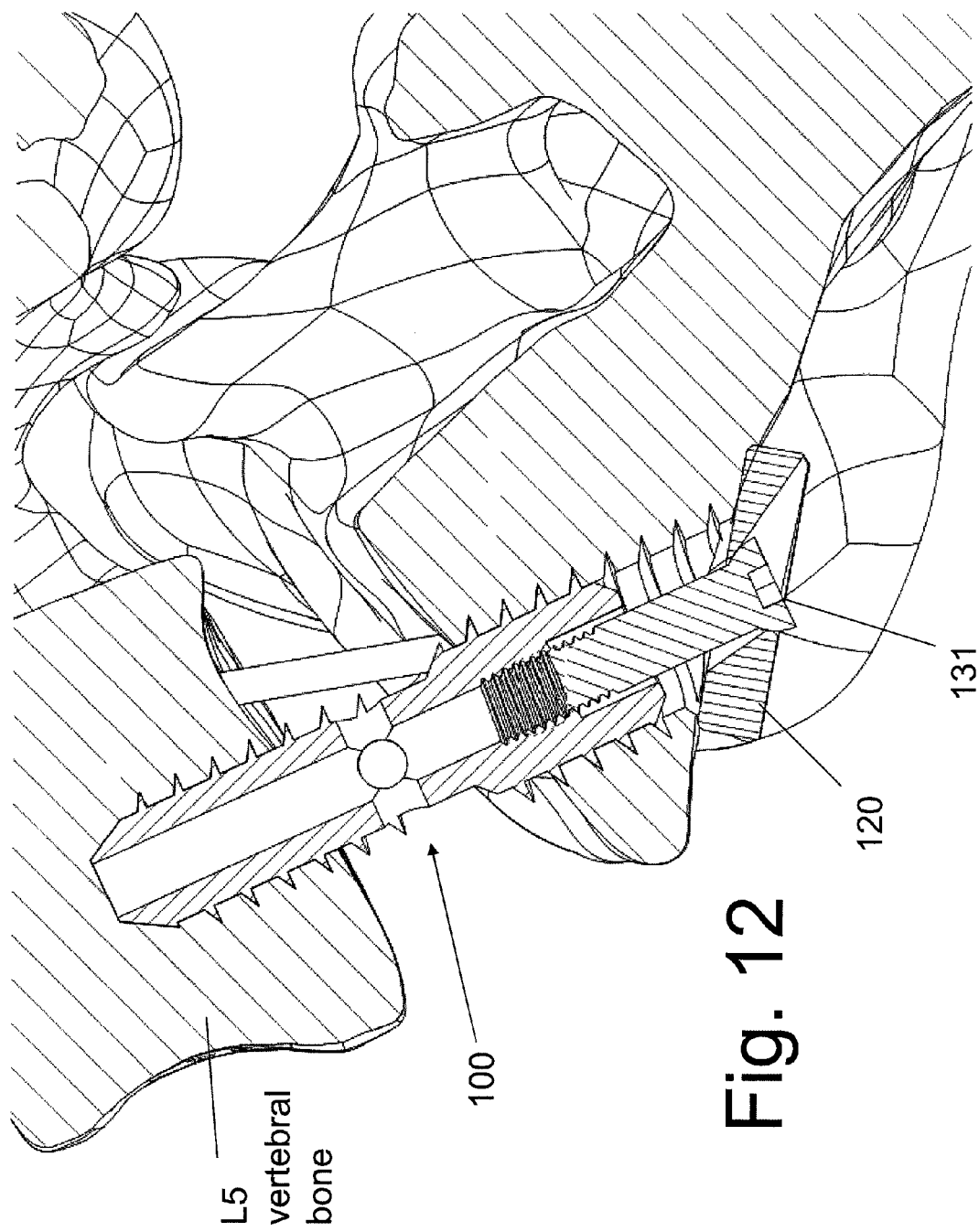
FIG. 12 shows an implanted screw.

In use, the bottom surface 1204 of the plate is adapted to rest against the anterior bony surface of the sacrum. Protrusions 128 are adapted to anchor into the anterior sacral surface and provide additional contact and fixation with the sacral bone. A threaded screw 131 is adapted to traverse the upper bore hole Y1 and engage threads 103 of bore 102 of screw 100 (see FIG. 12). Additional threaded screws 133 (with threads adapted to engage bone) are adapted to traverse at least one of the lower bore holes X1 and X2 and enter the sacral bone at the level of the S1 body. The screws 133 are further advanced across the L5/S1 disc space and into the L5 vertebral body. A central threaded bore hole Z rests within the center of plate 120, where bore Z is adapted to engage a threaded screw of plate cover 1222.

Figure 11B:
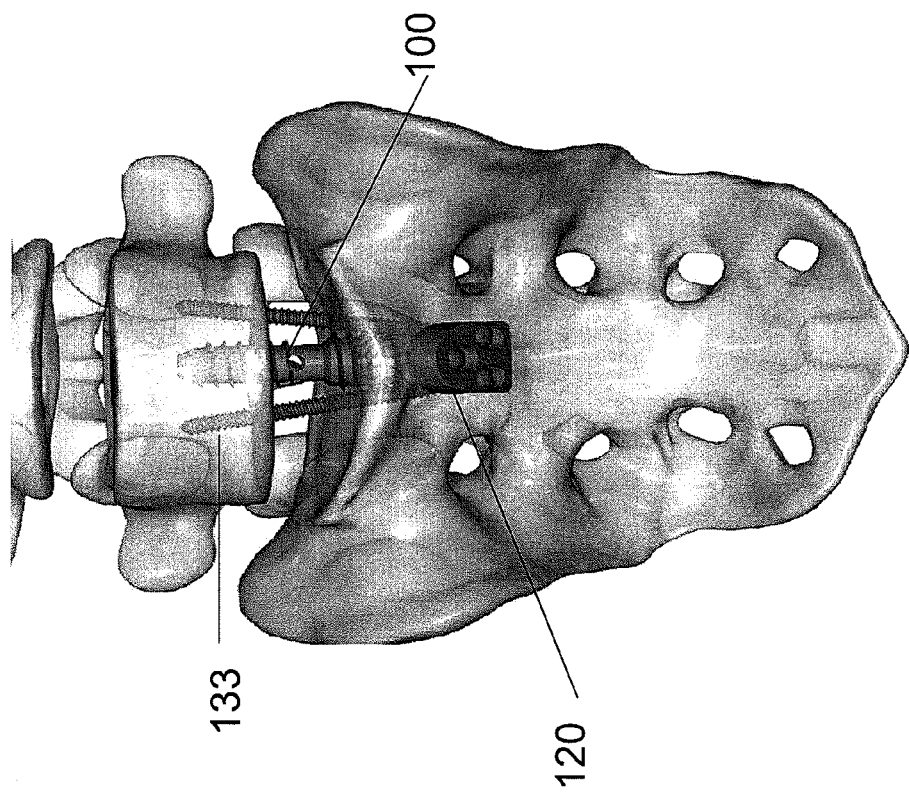
Figure 11A:
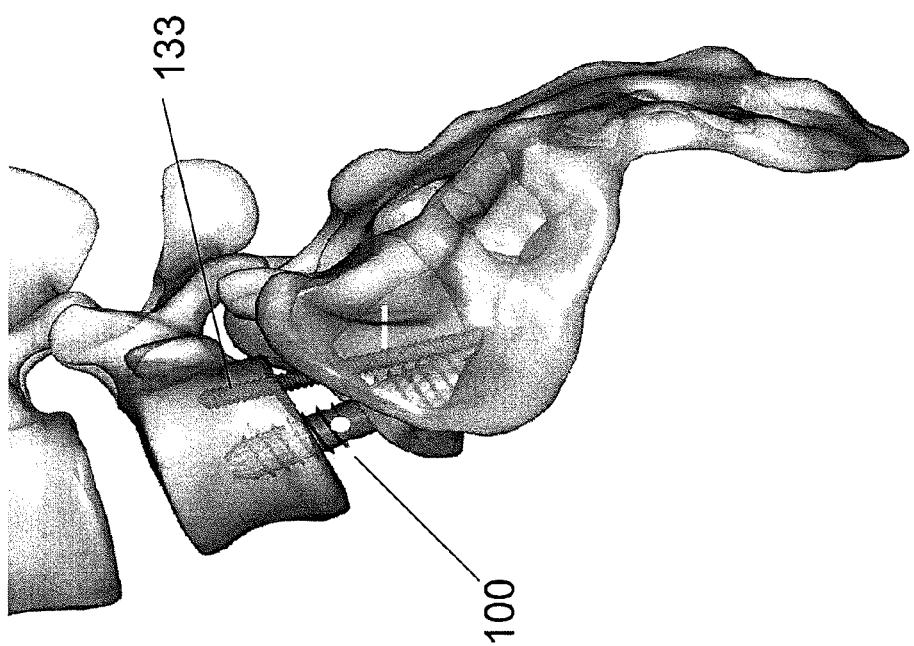

FIG. 10 shows the plate 120 implanted onto the surface of the anterior bony surface of the sacrum. Note that the sacral hole used to implant screw 100 is at least partially covered by a portion of the plate 120. A lateral view is shown in FIG. 11A and an anterior-posterior view is shown in FIG. 11B. These figures show diagrammatic representation of the implanted device and, for clarity of illustration, the vertebral bone and other aspects of the drawing are represented schematically. Those skilled in the art will appreciate that actual vertebral bones and sacrum may include anatomical details that are not shown in these figures. As suggested in the FIG. 11, the screws 133 are preferably positioned with the distal screws tips posterior to the screw heads, and wherein the distance between the distal screw tips is greater than the distance between the screw heads.

Figure 11C:
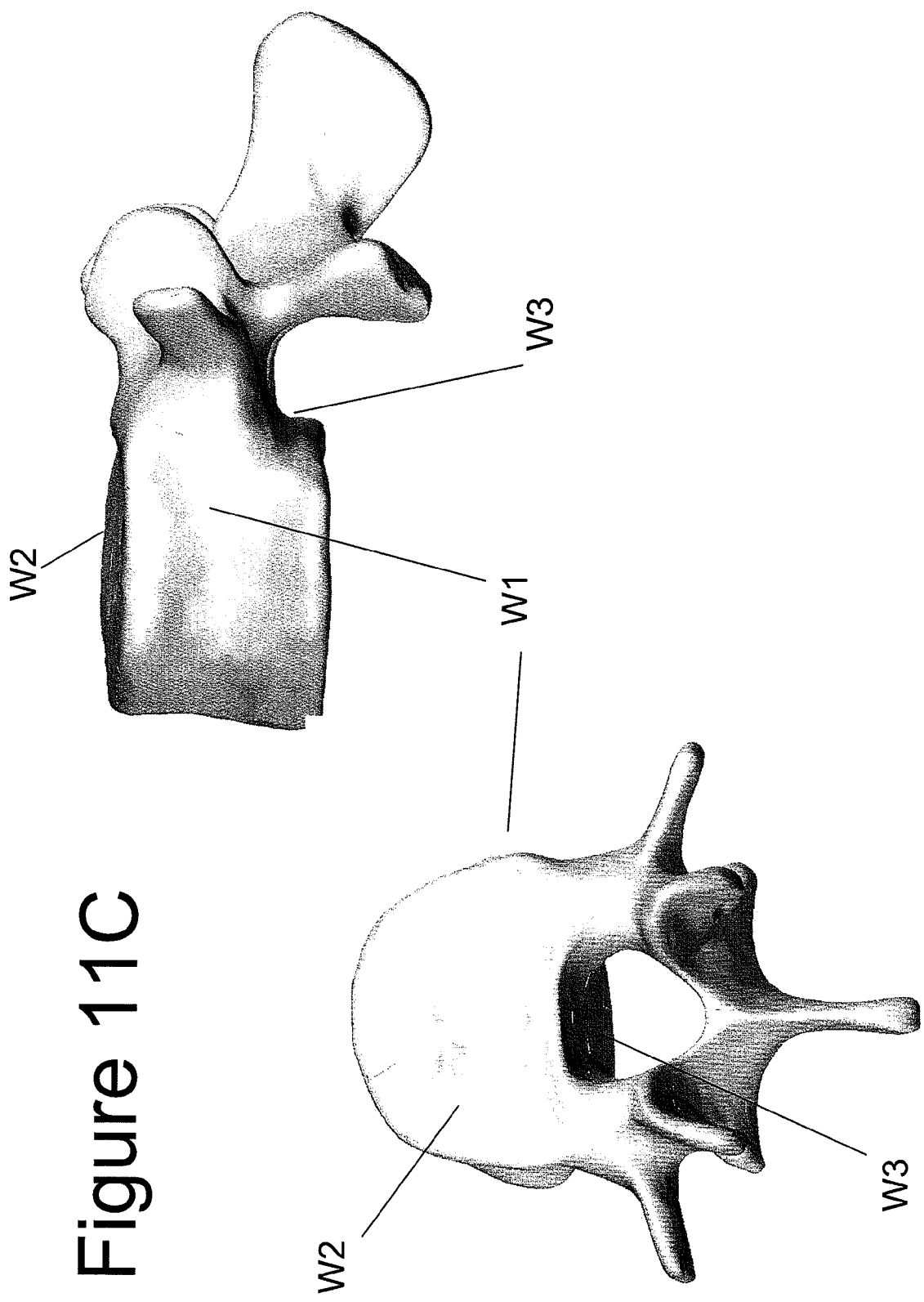
FIG. 11C illustrates a schematic representation of the L5 vertebra.

Since the internal aspect of the vertebral body contains bone that is less dense and less resistant to screw pull-out than an exterior wall of the vertebral body, the distal tips of screws 133 are preferably driven into the more dense surfaces of the exterior walls of the L5 vertebral body. For example, while not shown in the FIGS. 11A and 11B, the tips of screws 133 are preferably advanced until they penetrate and rest within a cortical surface of the L5 vertebral body. That is, the distal tips of screws 133 are preferably advanced into the lateral wall W1 of L5 vertebral body, or into the superior vertebral body surface W2 that abuts the L4/5 disc space, or into the posterior vertebral body surface W3. (FIG. 11C illustrates a schematic representation of the L5 vertebra. The surfaces W1-W3 are shown.) Alternatively, the distal screw tip may be advanced across the interface (FIG. 1) of the internal aspect of the L5 pedicle and the internal aspect of L5 vertebral body. That interface is known to have exceptional resistance to bone screw pull out.

Figure 13:
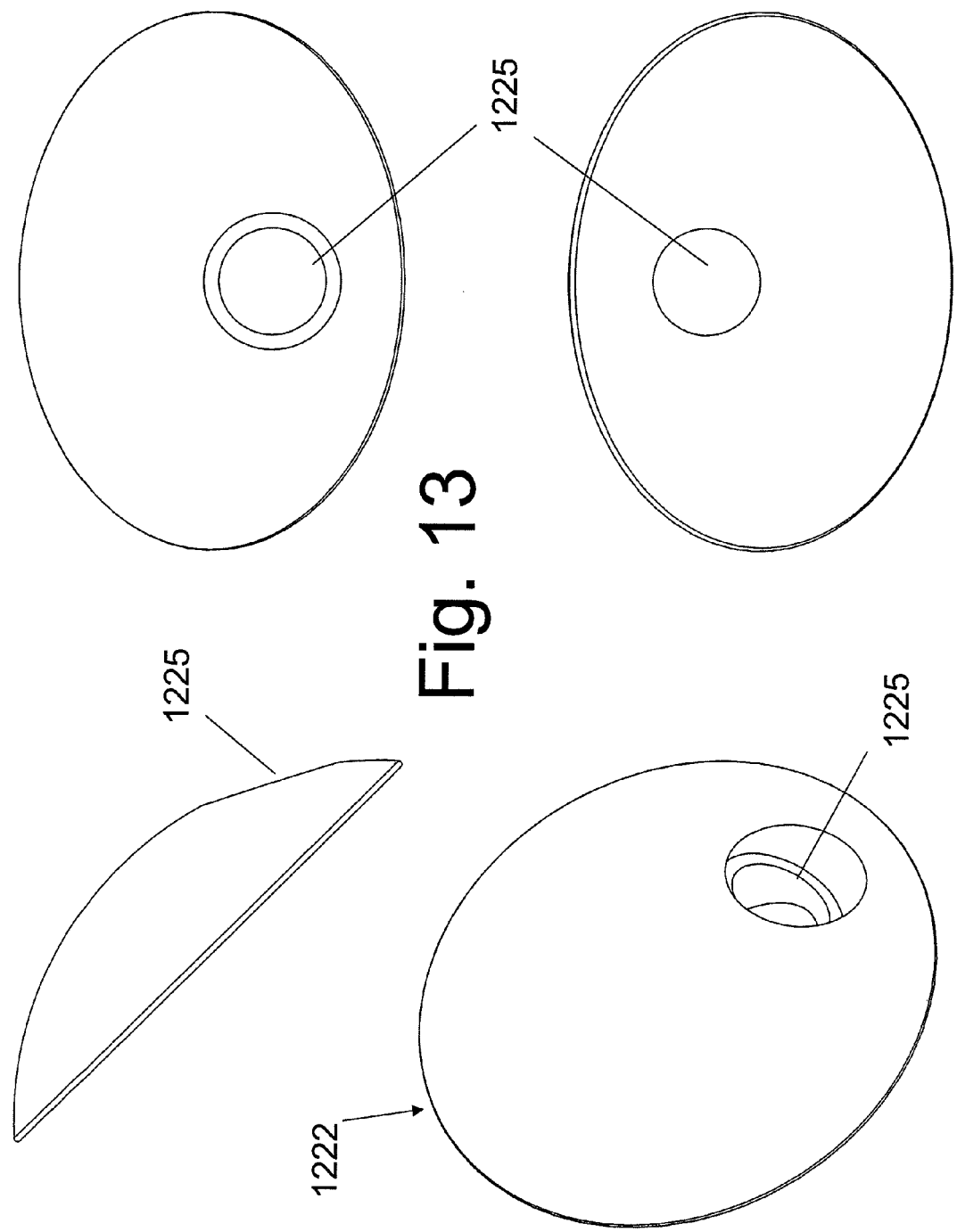
FIG. 13 shows a locking cover.

As an additional mechanism to strengthen the bony fixation provided by the plate and screw set, a locking mechanism is contemplated that would lock the head of screws 131 and 133 onto plate 120. This may be accomplished in a number of ways. In an embodiment, plate cover 1222 is used to forcibly capture and frictionally lock the head of screws 131 and 133 onto plate 120. Locking cover 1222 is shown in FIG. 13. Full thickness bore hole 1225 of cover 1222 is adapted to permit a locking screw to attach cover 1222 onto the bore hole Z of plate 120. As the threaded locking screw is advanced within the threaded bore hole Z of plate 120, the heads of screws 131 and 133 are immobilized between the plate cover 1222 and plate 120.

Figure 14:
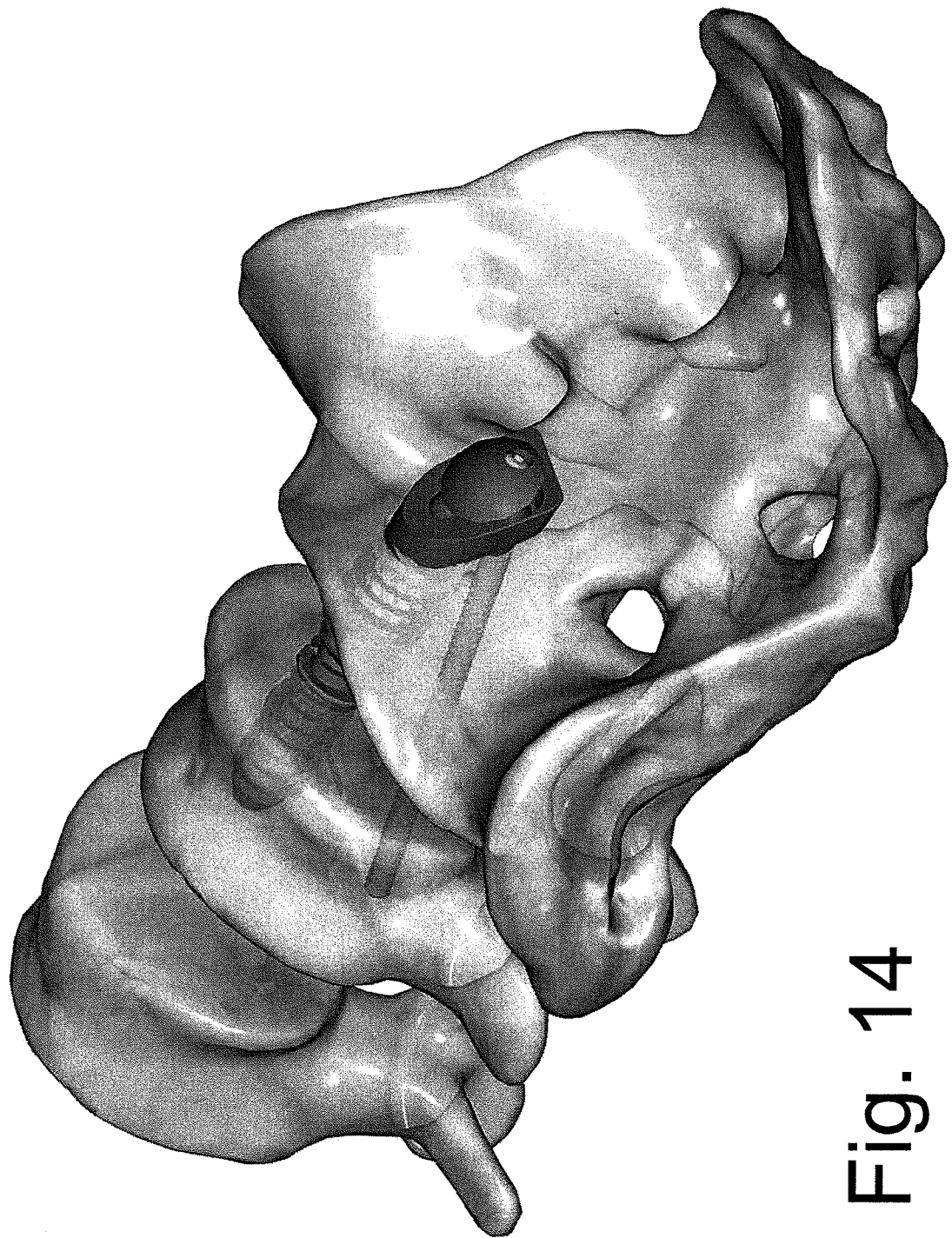
FIGS. 14 and 15 show a plate cover applied to a seated plate.
Figure 15:
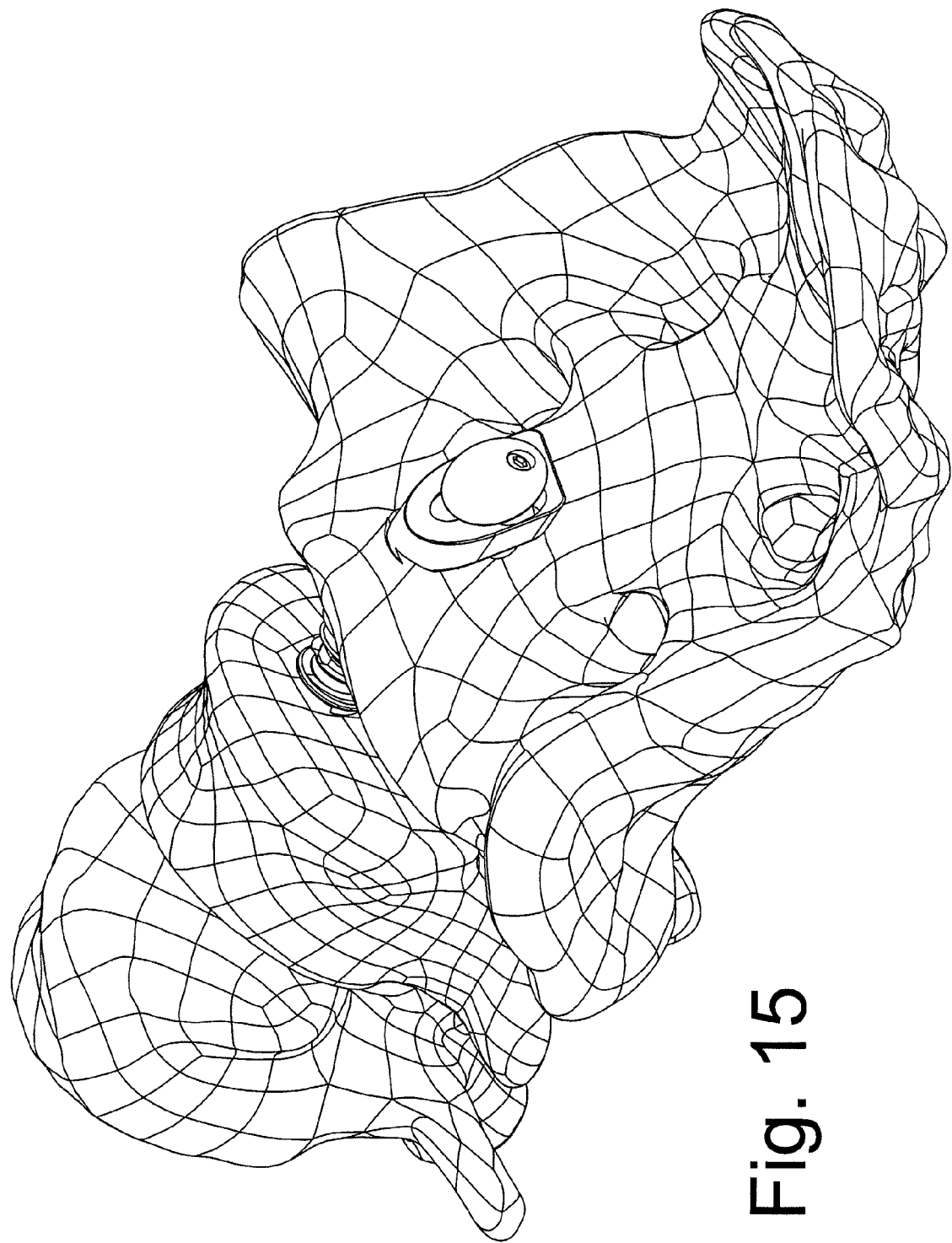
Figure 16:
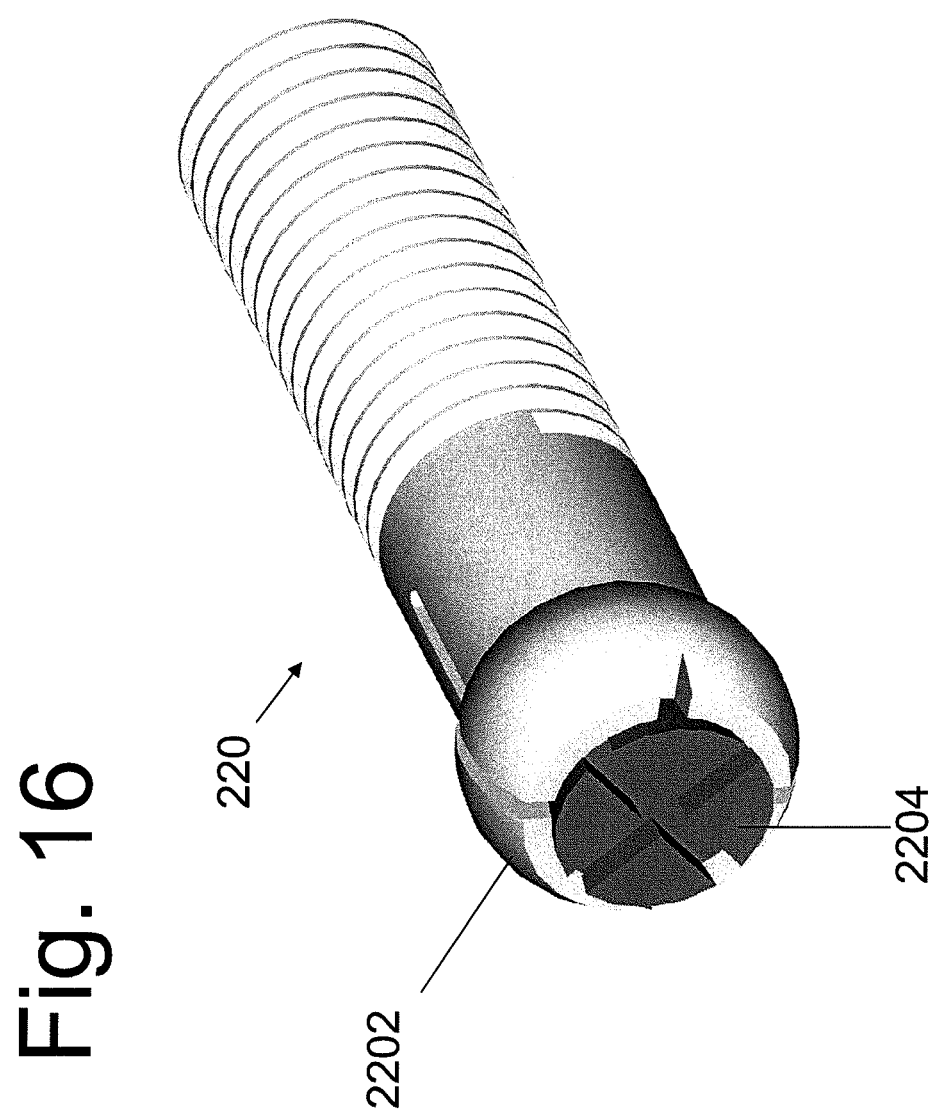
FIG. 16 shows an exemplary screw with an expandable head and locking screw.

FIGS. 14 and 15 show the plate cover 122 applied to seated plate 120. (FIG. 14 is a rendered illustration while FIG. 15 shows a line drawing.) Alternatively, each of screws 131 and 133 may be configured with an expandable head such that advancement of a locking screw within the expandable head of each screw 131 and 133 would outwardly expand the head of each of screw 131 and 133 and lock the screw head within the receiving bore hole of plate 120. An exemplary screw 220 with an expandable head 2202 and locking screw 2204 is shown in FIG. 16. Screws with expandable heads are well known in the art and have been used to lock bone screws to an orthopedic plate. U.S. Pat. No. 5,713,900 illustrates one such expandable head screw configuration. The patent is hereby incorporated by reference in its entirety.

It is a goal of the present disclosure to supplement the "AXLIF" procedure with additional fixation placed onto the sacrum and vertebral bodies of superior bones through a pre-sacral surgical corridor. In the preceding embodiments, a plate and bone screw assembly which has been implanted onto the anterior aspect of the sacrum using a pre-sacral surgical corridor is used to supplement the fixation of the "AXLIF" procedure. The pre-sacral surgical corridor designates a soft tissue corridor developed onto the anterior surface of the sacrum and extending from a skin incision at about the level of the coccyx and extending cephalad to at least the level of the S3 vertebral bone. The plate preferably attaches to the threaded screw 100 of the "AXLIF" procedure. The bone screws 133 are preferably anchored distally onto a rigid aspect/wall of the L5 vertebral body and attached proximally onto the plate using a plate/screw locking mechanism. While the invention has been illustrated for use in L5 to sacrum fixation, it is understood that the procedure can be similarly applied in L4 to sacrum fixation. In the latter, the bone screws 133 extend from the plate to the L4 vertebral body. As before, they preferably anchor distally onto a rigid aspect/wall of the L4 vertebral body (side walls, posterior body wall, superior body wall, inferior body wall and/or the internal aspect of the pedicle/vertebral body interface an the like) and attached proximally onto the plate using a plate/screw locking mechanism.

In an additional embodiment, fixation of a screw 133 onto a vertebral bone cephalad to the sacrum (such as L5, L4 or above) can be further enhanced by advancing an additional bone anchor into the superior bone and joining screw 133 to that anchor. Since the trajectory of the additional bone anchor may be different than that of a screw 133, the overall trajectory of the joined screw 133/additional anchor assembly will differ than that of screw 133 alone. This property can be advantageously used to place a screw 133 though a pre-sacral approach and have the distal aspect of the joined screw 133/ additional anchor assembly screw rest at a point that is posterior to the center of rotation (IAR) of the function spinal unit that is being fixated. This concept and method of use will be more fully discussed below.

Figure 17:
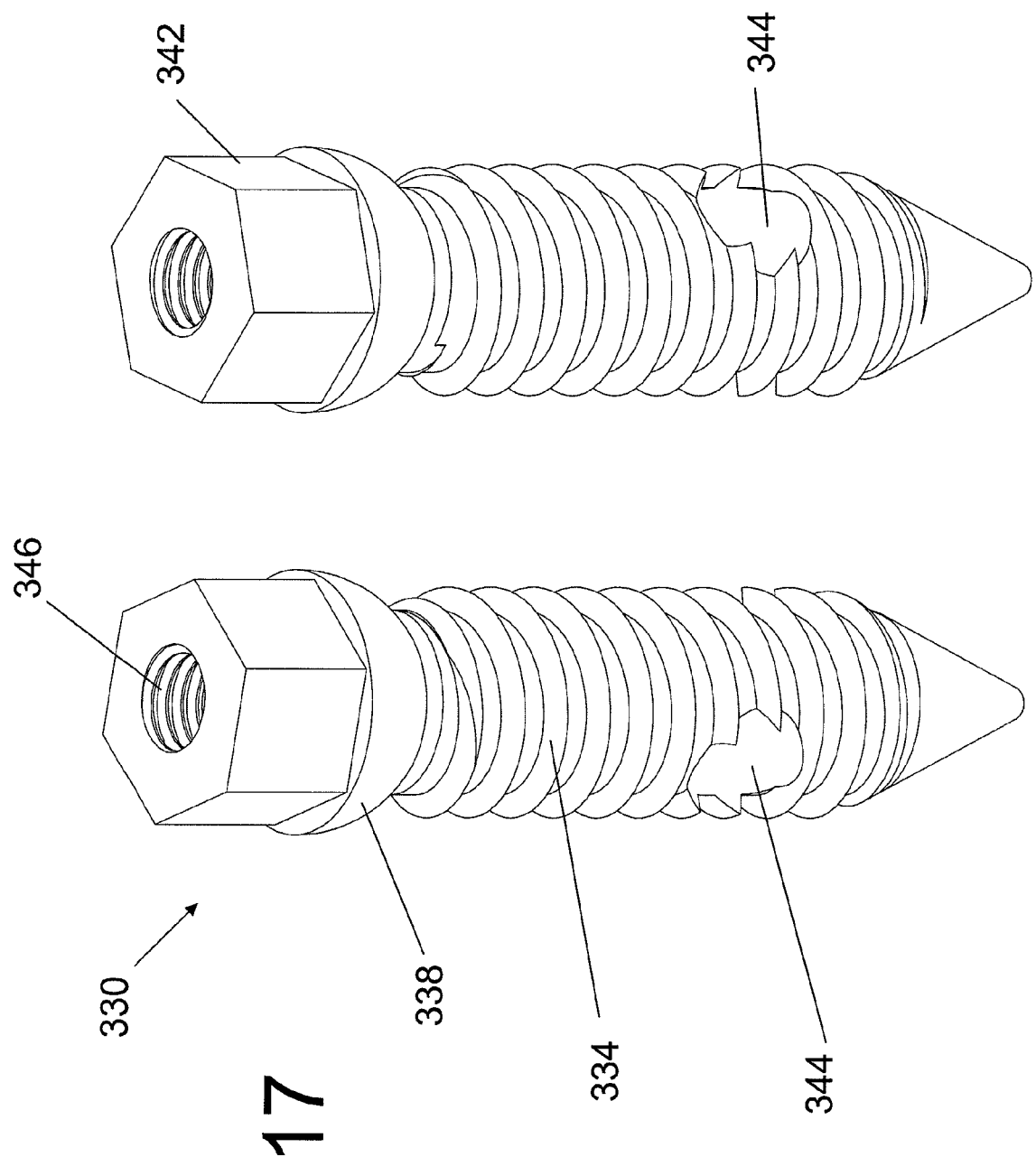
FIG. 17 shows a bone anchor.
Figure 18:
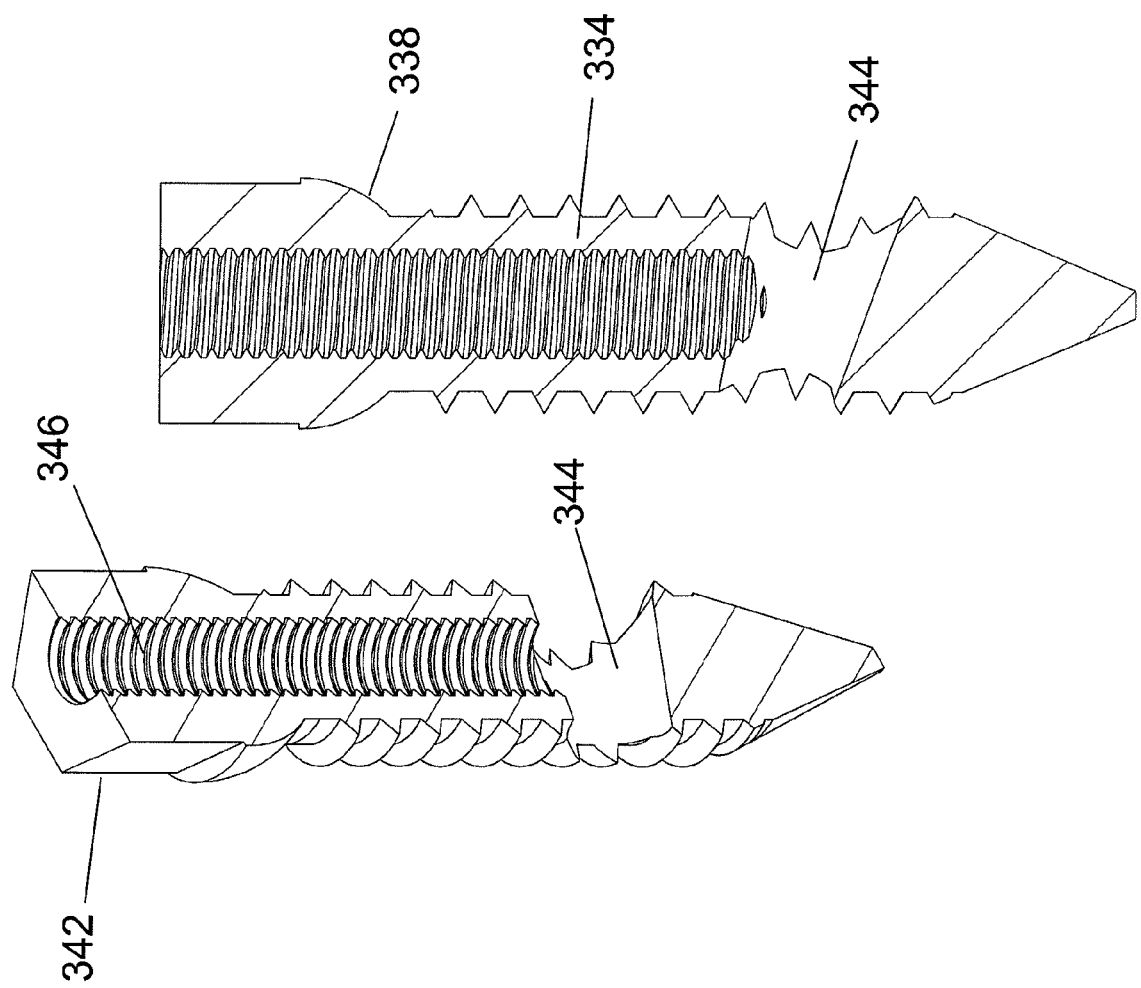
FIG. 18 shows sectional views of the bone anchor.

Anchor 330 is shown in FIG. 17 and in section views in FIG. 18. The anchor has threaded shank 334 with spherical head segment 338. A hexagonal segment 342 resides atop segment 338. Segment 342 is adapted to engage a complimentary screw driver with Hex-shaped indentation so that the screw driver can affix onto and drive the anchor 330 into bone. A bore hole 344 is placed across the threaded shank. A threaded bore hole 346 is placed along the long axis of anchor 330—as shown in FIG. 18. While the method of fixation and anchor 330 use is shown for L5 to sacrum fusion, it is understood that device and method may be similarly used to fixate L4 (and above levels) to the sacrum.

Figure 19:
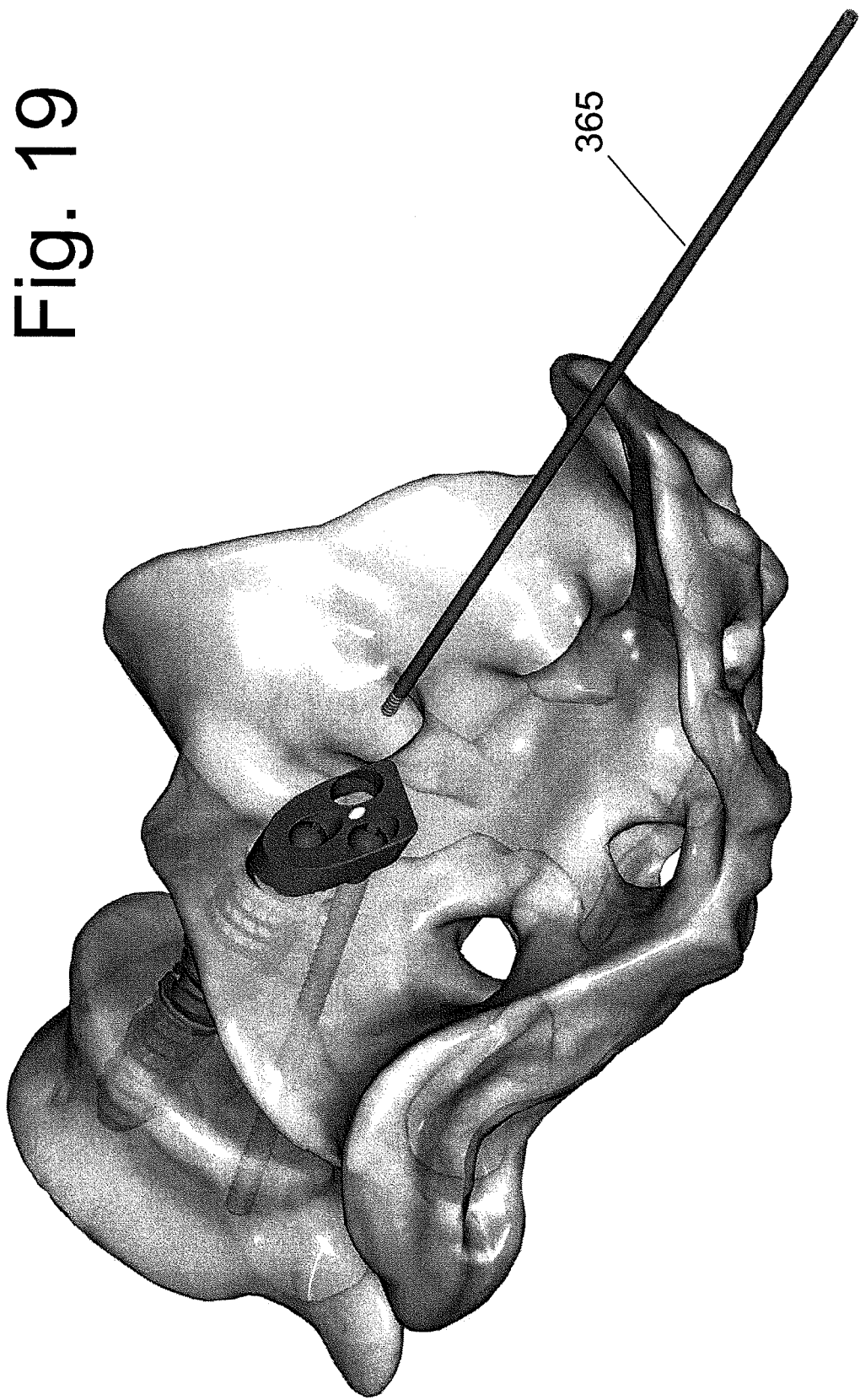
FIGS. 19 and 20 show the anchor advanced onto the left pedicle of L5 vertebra.

In use for L5 to sacrum fixation, anchor 330 is advanced into the pedicle portion of the L5 vertebral bone using a posterior surgical corridor so that the shank 334 enters the vertebral bone at approximately location 811 (FIG. 1). Preferably, the anchor 330 is advanced until segment 338 rests against the pedicle entry point 811. Preferably, the procedure is performed in a percutaneous manner and under X-ray guidance/visualization. Anchor 330 is advanced so that bore 344 is positioned within the vertebral body and immediately distal to the body/pedicle interface (that is, the shank of anchor 330 has traversed the body/pedicle interface and entered the vertebral bone). A jig or surgical guide (not shown) is attached onto the segment 342 (using threads 346) and used to guide the distal aspect of screw 133 to bore 344 of anchor 330. In FIG. 19, anchor 330 had already been advanced onto left pedicle of L5 (the pedicle and screw are hidden in FIG. 19 and shown in FIG. 20). A wire 365 is guided by the surgical guide so that the distal end of the wire traverses bore X2 of the plate 120 and is advanced into bore hole 344 of shank 334 of anchor 330.

Figure 20:
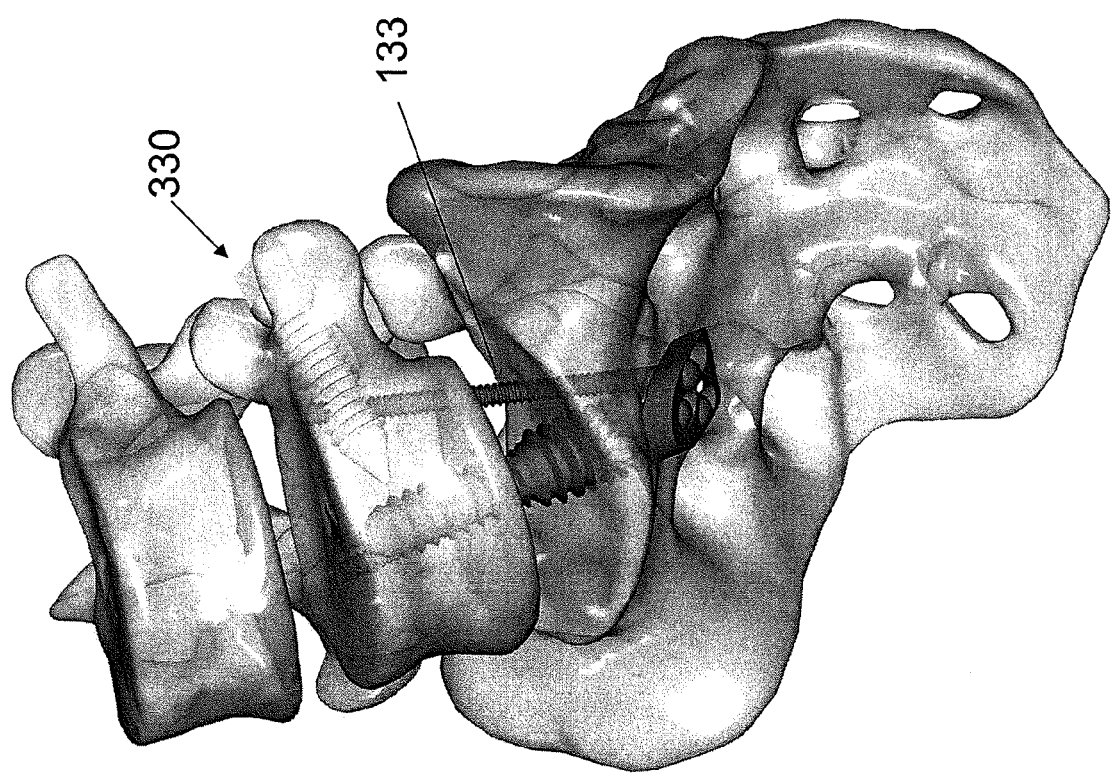
Figure 21:
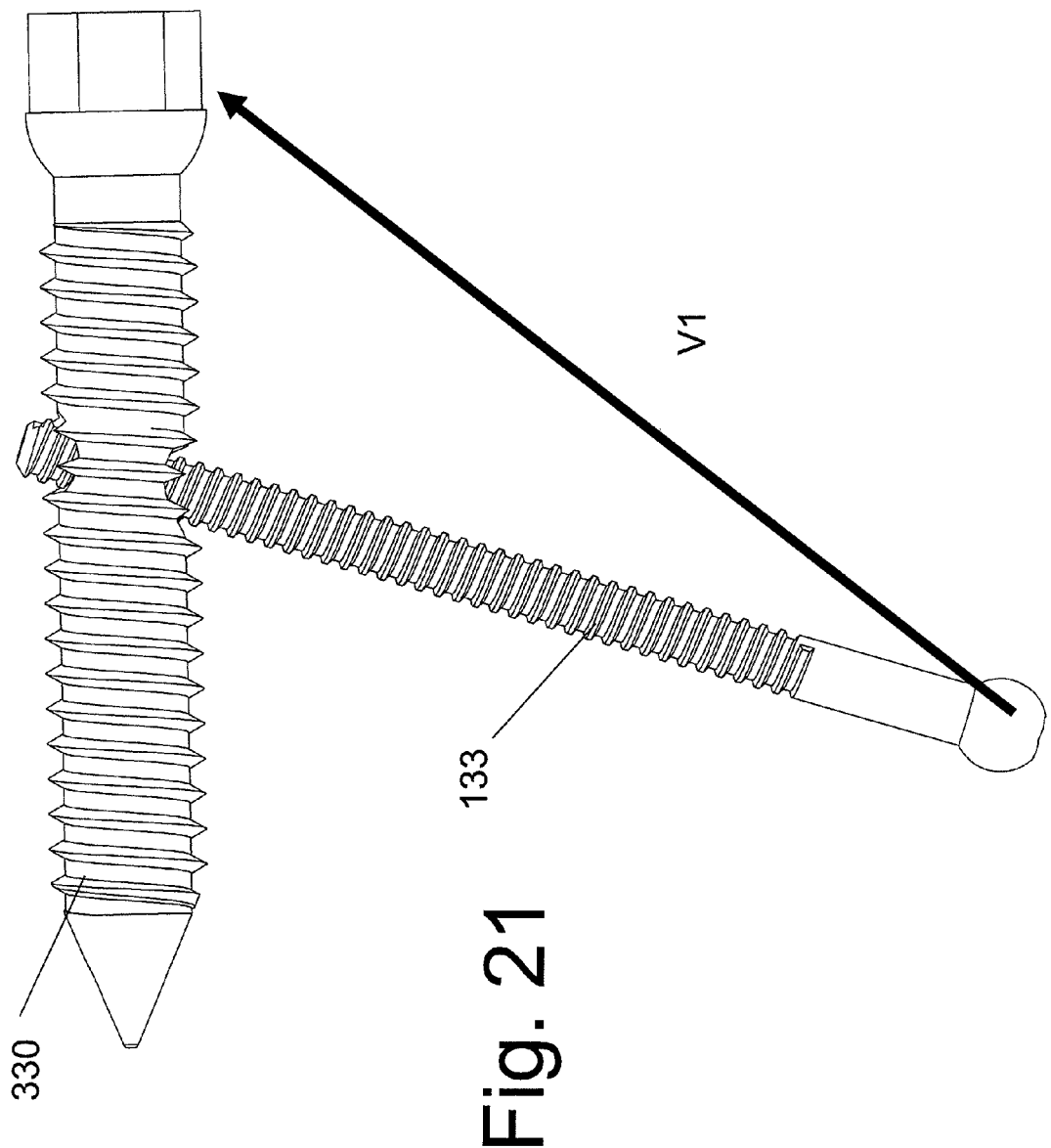
FIG. 21 shows a joined screw and an additional anchor assembly without the bone elements.

Screw 133 has central bore 1330 adapted to accept wire 365. Screw 133 is rotated and advanced over wire 365 until the distal end resides within bore 344 of anchor 330. The placed screw 133 is shown in FIG. 20. For clarity of illustration, FIG. 21 shows the joined screw 133/additional anchor 330 assembly without the bone elements. Sectional views are shown in FIG. 22. After the distal of screw 133 is passed into bore 344 of anchor 330, set screw 372 is tightened so as to rigidly retain 133 within bore 344.

With reference to FIG. 21, the joined screw 133/additional anchor 330 assembly forms a fixation assembly with the effective trajectory of vector V1. Thus, screw 133 can be placed into the sacrum through a pre-sacral approach and traverse the L5/S1 disc space anterior to the center of rotation (see IAR in FIG. 1) but, when coupled to anchor 330, can form an effect anchor assembly that traverses the disc space (in trajectory V1) posterior to the IAR. In this way, screw 100 traverses the L5/S1 disc space anterior to the IAR while a first screw 133/additional anchor 330 assembly attached to bore X1 of plate 120 (using a screw to plate locking mechanism) will traverse the L5/S1 disc space posterior to the IAR and a second screw 133/additional anchor 330 assembly attached to bore X2 of plate 120 will also traverse the L5/S1 disc space posterior to the IAR. This forms a three point fixation configuration around the IAR of the disc space to be fixated.

While the preceding embodiment has be illustrated for L5 to sacral fusion, it is understood that the same devices and method can be used at fixate the L4 vertebral bone to the sacrum. In that embodiment, an additional anchor 330 is advanced into each of the two pedicle portions of the L4 vertebral bone. A screw 133 is placed through each of bores X and guided to bore 344 of the corresponding anchor 330 using a surgical guide and wire 365 as previously described. The set screw 372 of each anchor 330 is tightened after placement of screw 133. The proximal aspect of each screw 133 is also locked to plate 120 (which is in turn affixed to screw 100 via screw 131 and bore Y) by a screw to plate locking mechanism.

The preceding disclosure teaches multiple embodiments to supplement the bone fixation strength of the "AXLIF" procedure by placing a plate and screw assembly that has been placed through a pre-sacral surgical corridor. While describe as separate embodiments, the various mechanisms may be used in combinations to produce additional assemblies that have not been specifically described herein, but, nevertheless, would fall within the scope of this invention.

The disclosed devices or any of their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with nanotube materials to further impart unique mechanical or biological properties. In addition, any components may be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method for fixation of a sacrum with at least an immediately superior vertebral bone, comprising:
    creating a first borehole into an anterior cortical bone surface of said sacrum;
    advancing a first fixation post through said first borehole, said sacrum, and a disc space immediately superior to said sacrum, and into said immediately superior vertebral bone;
    creating a second borehole in said anterior cortical bone surface of said sacrum, said second borehole being different than said first borehole;
    advancing a second fixation post through said second bore hole, said sacrum, and said disc space, and into said immediately superior vertebral bone; and
    connecting a proximal aspect of said first fixation post with a proximal aspect of said second fixation post, said connected proximal aspects of each of said first and second fixation posts configured to be positioned at least partially outside of said anterior cortical bone surface of said sacrum.

2. The method of claim 1, wherein a trajectory of said first fixation post diverges within said sacrum relative to a trajectory of said second fixation post.

3. The method of claim 1, wherein said immediately superior vertebral bone comprises an L5 vertebral bone.

4. The method of claim 3, wherein said second fixation post is configured to at least partially engage a cortical surface of a side wall of said L5 vertebral bone.

5. The method of claim 3, wherein said second fixation post is configured to at least partially extend into an L4 vertebral bone.

6. The method of claim 3, wherein a third fixation post is advanced through said sacrum, said disc space, and into said L5 vertebral bone.

7. The method of claim 6, wherein a trajectory of said first fixation post diverges within said sacrum relative to a trajectory of said second fixation post.

8. The method of claim 6, wherein said third fixation post is configured to at least partially engage a cortical surface of a side wall of said L5 vertebral bone.

9. The method of claim 6, wherein said third fixation post is configured to at least partially extend into an L4 vertebral bone.

10. The method of claim 6, wherein a proximal aspect of said third fixation post is connected to a proximal segment of said first and second fixation posts.

11. The method of claim 10, wherein said proximal aspect of said third fixation post is configured to be positioned at least partially outside of said anterior cortical bone surface of said sacrum.

12. A method for fixation of a sacral bone with at least one superior vertebral bone, comprising:
  advancing a first fixation member through a pedicle portion of said superior vertebral bone from a posterior to an anterior trajectory, a distal end of said first fixation member being positioned within a body of said superior vertebral bone;
  creating a borehole in an anterior cortical bone surface of said sacral bone;
  advancing a second fixation member through said borehole, through said sacral bone, a disc space immediately superior to said sacral bone, and into said superior vertebral bone; and
  affixing a distal segment of said first fixation member with a distal segment of said second fixation member within said superior vertebral bone.

13. The method of claim 12, wherein a trajectory of said first fixation post diverges within said superior vertebral bone relative to a trajectory of said second fixation post.

14. The method of claim 12, wherein said superior vertebral bone comprises an L5 vertebral bone.

15. The method of claim 12, wherein said superior vertebral bone is an L4 vertebral bone.

16. The method of claim 12, wherein said first fixation post is advanced through an interface of said body of said superior vertebral bone to a pedicle thereof.

17. The method of claim 12, wherein said second fixation post is guided to said first fixation post using a surgical jig.

18. The method of claim 12, wherein said second fixation post is advanced to a position of said first fixation post using a guide wire.

19. The method of claim 12, wherein a proximal aspect of said second fixation post is configured to be positioned at least partially outside of said anterior cortical bone surface of sacral bone.

20. The method of claim 12, wherein a locking feature rigidly affixes a distal segment of said first fixation post and a distal segment of said second fixation post.

21. The method of claim 12, wherein said method is performed bilaterally.

22. The method of claim 12, wherein said method is performed in a percutaneous manner.

* * * * *